US007393640B2

(12) United States Patent
Kumar et al.

(10) Patent No.: US 7,393,640 B2
(45) Date of Patent: Jul. 1, 2008

(54) TERMINAL-PHOSPHATE-LABELED NUCLEOTIDES WITH NEW LINKERS

(75) Inventors: Shiv Kumar, Belle Mead, NJ (US); Mark McDougall, Arroyo Grande, CA (US); Anup Sood, Flemington, NJ (US); John Nelson, Hillsborough, NJ (US); Carl Fuller, Berkeley Heights, NJ (US); John Macklin, Wenonah, NJ (US); Paul Mitsis, Trenton, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 502 days.

(21) Appl. No.: 10/772,996

(22) Filed: Feb. 5, 2004

(65) Prior Publication Data

US 2004/0241716 A1    Dec. 2, 2004

Related U.S. Application Data

(60) Provisional application No. 60/445,189, filed on Feb. 5, 2003.

(51) Int. Cl.
*C12Q 1/68* (2006.01)
*C12P 19/34* (2006.01)

(52) U.S. Cl. .......................................... 435/6; 435/91.1
(58) Field of Classification Search ........................ None
See application file for complete search history.

(56) References Cited

U.S. PATENT DOCUMENTS

| | | | | |
|---|---|---|---|---|
| 6,232,075 | B1 * | 5/2001 | Williams | 435/6 |
| 6,323,186 | B1 | 11/2001 | Klaubert et al. | |
| 6,399,335 | B1 | 6/2002 | Kao et al. | |
| 2003/0064366 | A1 * | 4/2003 | Hardin et al. | 435/6 |

FOREIGN PATENT DOCUMENTS

| | | |
|---|---|---|
| WO | WO00/36152 | 6/2000 |
| WO | WO03/020734 | 3/2003 |
| WO | WO03/020891 | 3/2003 |
| WO | WO03/020984 | 3/2003 |

OTHER PUBLICATIONS

Schweins et al. ("The role of the metal ion in the p21ras catalysed GTP-hydrolysis: Mn2+ versus Mg2+" J Mol Biol. Mar. 7, 1997;266(4):847-56).*
Tabor et al. (Effect of manganese ions on the incorporation of dideoxynucleotides by bacteriophage T7 DNA polymerase and *Escherichia coli* DNA polymerase I Proc Natl Acad Sci U S A. Jun. 1989;86(11):4076-80).*
Yarbrough et al. ("Synthesis and properties of fluorescent nucleotide substrates for DNA-dependent RNA polymerases" J Biol Chem. Dec. 10, 1979;254(23):12069-73).*
Wu et al. ("Synthesis and properties of adenosine-5'-triphosphoro-gamma-1-(5-sulfonic acid)naphthyl ethylamidate: a fluorescent nucleotide substrate for DNA-dependent RNA polymerase from *Escherichia coli*" Arch Biochem Biophys. May 1, 1986;246(2):564-71).*
Bernard et al. ("Synthesis of complementary RNA on RNA templates using the DNA-dependent RNA polymerase of *Escherichia coli*" Biochim Biophys Acta. Oct. 18, 1977;478(4):407-16).*
McGuigan et al. ("DNA fingerprinting by sampled sequencing" Methods Enzymol. 1993;218:241-58).*
Tabor et al. ("Effect of manganese ions on the incorporation of dideoxynucleotides by bacteriophage T7 DNA polymerase and *Escherichia coli* DNA polymerase I" Proc Natl Acad Sci U S A. Jun. 1989;86(11):4076-80).*
Yarbrough, L., et al., "Synthesis and Properties of Fluorescent Nucleotide Substrates for DNA-Dependent RNA Polymerases", *The Journal of Biological Chemistry*, vol. 254, No. 23, 1979, p. 12069-12073.
Conyers, G. B., Wu, G, Bessman, M. J. & Mildvan, A. S. (2000). "Metal Requirements of a Diadenosine Pyrophosphatase from *Bartonella bacilliformis*: Magnetic Resonance and Kinetic Studies of the Role of Mn2+". Biochemistry, 39(9), 2347-2354.
Günther Sillero, M. A., Socorro, S., Baptista, M. J., Del Valle, M., De Diego, A. & Sillero, A. (2001). "Poly(A) polymerase from *Escherichia coli* adenylylates the 3'-hydroxyl residue of nucleosides, nucleoside 5'-phosphates and nucleosides(5')oligophospho(5')nucleosides (NpnN)". European Journal of Biochemistry, 268(12), 3605-3611.
Ho, C. K., Pei, Y. & Shuman, S. (Dec. 18, 1998). "Yeast and Viral RNA 5' Triphosphatases Comprise a New Nucleoside Triphosphatase Family". Journal of Biological Chemistry, 273(51) 34151-34156.
Tabor, S. & Richardson, C. C. (Jun. 1, 1989). "Effect of Manganese Ions on the Incorporation of Dideoxynucleotides by Bacteriophage T7 DNA Polymerase and *Escherichia coli* DNA Polymerase I". PNAS, 86(11), 4076-4080.
Tanner, J. A., Abowath, A. & Miller, A. D. (Feb. 1, 2002). "Isothermal Titration Calorimetry Reveals a Zinc Ion as an Atomic Switch in the Diadenosine Polyphosphates". Journal of Biological Chemistry, 277(5), 3073-3078.
Yarbrough, L. R., Schlageck, J. G. & Baughman, M. (Dec. 1979). "Synthesis and properties of fluorescent nucleotide substrates for DNA-dependent RNA polymerases". Journal of Biological Chemistry, 254 (23), 12069-12073.

* cited by examiner

*Primary Examiner*—Kenneth R. Horlick
*Assistant Examiner*—Christopher M. Babic
(74) *Attorney, Agent, or Firm*—Yonggang Ji

(57) ABSTRACT

The present invention describes methods of using terminal-phosphate-labeled nucleotides in the presence of a manganese salt to enhance their substrate properties towards various enzymes. Particularly described are methods of detecting a nucleic acid in a sample, based on the use of terminal-phosphate-labeled nucleotides as substrates for nucleic acid polymerases, in the presence of a manganese salt. Further provided are manganese complexes of terminal-phosphate-labeled nucleotides as well as terminal-phosphate-labeled nucleotides with new linkers with enhanced substrate properties.

10 Claims, 9 Drawing Sheets

The Effect of Mg and Mn ions on the incorporation of base labeled nucleotides and phosphate labeled nucleotides Incorporation rate vs. MnCl$_2$ concentration, at 5 mM MgCl$_2$, based on change in slope of REG fluorescence

No misincorporation of dCTP-DAH-ROX by Phi 29 exo⁻ using $Mn^{++}$ (at saturating dCTP-ROX, 25 µM)

45  35  25  15  10  5  2  1.5  0.5  0  P/T   time (min)

Primer/template
5'-Cy5...ATCCG
3'- .....TAGGCGACTG...

Incorporation of dT4P-DDAO by different polymerases in the presence of Mn2+, Mg2+ and both Mn2+ and Mg2+

TERMINAL-PHOSPHATE-LABELED NUCLEOTIDES WITH NEW LINKERS

CROSS REFERENCE TO RELATED APPLICATIONS

This application claims priority to U.S. provisional application No. 60/445,189 filed Feb. 5, 2003; the disclosures of which are incorporated herein by reference in their entirety.

BACKGROUND OF THE INVENTION

1. Field of the Invention

The present invention relates generally to the use of terminal-phosphate-labeled nucleotides with three or more phosphates as substrates for various enzymes including nucleic acid polymerases in the presence of $Mn^{++}$ as cofactor for enhanced activity. The labels employed are chemiluminescent, fluorescent, electrochemical and chromogenic moieties as well as mass tags and include those that are directly detectable, as well as those that are detectable after enzyme activation or feed into other processes to generate a different signal. These terminal phosphate labeled nucleotides could be used in homogenous assays including identification of specific genotypes or genetic sequences. Further provided are new terminal phosphate labeled nucleoside polyphosphates with linkers that connect the label to the terminal phosphate of the nucleotides to enhance their substrate properties, i.e. to increase their rate of utilization by different enzymes.

2. Description of Related Art

A number of enzymes utilize or act on nucleoside triphosphates and their analogs. These enzymes include ligases, nucleic acid polymerases, phosphodiesterases, phosphorylases, kinases and phosphatases. All these enzymes require certain metal ions as cofactors and although many of these enzymes can work in the presence of different metal ions, one metal is generally more favored than the rest.

Nucleic acid polymerases are enzymes which catalyze the polymerization of nucleoside 5'-triphosphates to form DNA or RNA. They include DNA dependent DNA polymerases, DNA dependent RNA polymerases and RNA dependent DNA polymerases. These enzymes require the presence of a divalent metal ion as cofactor, typically $Mg^{2+}$, although it is known that $Mn^{2+}$ and even $Ca^{2+}$ can sometimes substitute for the $Mg^{2+}$. With normal nucleotides, the rate of reaction is greater when $Mg^{2+}$ is used than it is with other metals.

There have been numerous nucleotide analogs made which can also serve as substrates for nucleic acid polymerases, including compounds that have, for example, fluorescent labels. These labels have been attached to the base portion of the nucleotide, and in rare cases to the sugar portion of the nucleotide. These have worked as substrates for polymerases more or less under the same reaction conditions with the same divalent metal ion cofactors as the normal, unsubstituted nucleotides.

There is also interest in the use of nucleotides labeled on the gamma phosphate position. A number of γ-phosphate labeled nucleoside triphosphates are commercially available from Molecular Probes (U.S. Pat. No. 6,323,186). In these nucleotides the dye (bodipy) is attached to the y-phosphate through a phosphorothioate linkage. U.S. Pat. No. 6,399,335 entitled 'γ-phosphoester nucleoside triphosphates' provides methods and compositions for polymerizing particular nucleotides with a polymerase using y-phosphoester linked nucleoside triphosphates. A number of other patent applications from LI-COR Inc. (U.S. Pat. No. 6,232,075; US 2003/0194740: WO 01/94609; and US 2003/0186255) describes the synthesis and methods of use of different base and γ-phosphate labeled nucleoside-5'-triphosphates. Using these nucleotides with DNA polymerase can lead to identification of specific nucleotides in a DNA or RNA sequence by identification of the labeled pyrophosphate released upon incorporation of the nucleotide base into RNA or DNA.

Methods are known for detecting specific nucleic acids or analytes in a sample with high specificity and sensitivity. Such methods generally require first amplifying nucleic acid sequence based on the presence of a specific target sequence or analyte. Following amplification, the amplified sequences are detected and quantified. Conventional detection systems for nucleic acids include detection of fluorescent labels, fluorescent enzyme-linked detection systems, antibody-mediated label detection, and detection of radioactive labels.

One disadvantage of these methods is that the labeled product not only requires some type of separation from the labeled starting materials but also since the label is attached to the product, it is different than the natural product to be identified. It would, therefore, be of benefit to use methods and substrates that form unmodified product and at the same time generate a signal characteristic of the reaction taking place. It is of further benefit if the signal generated doesn't require separation from the starting materials but even if a separation is required benefits of generating unmodified product in many cases are overwhelming.

Gamma phosphate labeled nucleotides do provide such an opportunity. For example, incorporation of gamma phosphate labeled nucleotides into DNA or RNA by nucleic acid polymerases results in the production of unmodified DNA or RNA and at the same time the labeled pyrophosphate generated is used to detect, characterize and/or quantify the target. These nucleotides, however, are very poor substrates for various nucleic acid polymerases and it would, therefore be of benefit to improve the rate of incorporation of these terminal-phosphate labeled nucleotides. As demonstrated earlier (WO 03/020891; WO 03/020984; WO 03/020734) some rate enhancement can be achieved by increasing the length of polyphosphate chain between the label and the nucleotide. This rate enhancement although useful for some applications, for practical reasons is still insufficient for many applications where several hundred nucleotides have to be added in a short time, e.g. PCR.

It would, therefore, be of benefit to further enhance the rate of utilization of terminal phosphate labeled nucleotides. This and other concerns are addressed below.

SUMMARY OF THE INVENTION

The present invention provides several methods of use, and compositions to enhance the usefulness of terminal-phosphate labeled nucleotides (also referred to as terminal-phosphate labeled nucleoside polyphosphates). Current invention provides methods of using manganese salts in conjunction with terminal phosphate labeled nucleotides in enzymatic reactions to enhance their use by enzymes over and beyond what is observed in the absence of manganese even if other metal salts are present. Also provided are new composition of matter in the form of terminal-phosphate labeled nucleotides with linkers that enhance their substrate properties.

The present invention provides a method of increasing the rate of an enzyme catalyzed nucleoside monophosphate transfer from a terminal-phosphate-labeled nucleoside polyphosphate to detect the activity of said enzyme or said terminal-phosphate-labeled nucleoside polyphosphate, said method comprising: conducting said enzyme catalyzed nucleoside monophosphate transfer from a terminal-phosphate-labeled nucleoside polyphosphate reaction in reaction buffer comprising a manganese salt, thereby increasing the rate of said reaction over the rate of said reaction in the absence of manganese even if other divalent metal salts were present in the buffer.

The present invention provides for a method of detecting the presence of a nucleic acid sequence including the steps of: a) conducting a nucleic acid polymerase reaction in the presence of a manganese salt to increase the rate of utilization of terminal-phosphate-labeled nucleoside polyphosphates, said polymerase reaction including reacting a terminal-phosphate-labeled nucleotide, and producing labeled polyphosphate; b) permitting the labeled polyphosphate to react with a phosphatase to produce a detectable species; and c) detecting the presence of the detectable species. A definition of phosphatase in the current invention includes any enzyme which cleaves phosphate mono esters, polyphosphates and nucleotides to release inorganic phosphate. In the context of the present invention, this enzyme does not cleave a terminally labeled nucleoside phosphate (i.e. the terminal-phosphate-labeled nucleotide is substantially non-reactive to phosphatase). The phosphatase definition herein provided specifically includes, but is not limited to, alkaline phosphatase (EC 3.1.3.1) and acid phosphatase (EC 3.1.3.2). The definition of a nucleotide in the current invention includes a natural or modified nucleoside phosphate.

The invention further provides for a method of detecting the presence of a DNA sequence including the steps of: a) conducting a DNA polymerase reaction in the presence of a terminal-phosphate-labeled nucleotide and a manganese salt to increase the rate of utilization of terminal-phosphate-labeled nucleoside polyphosphates, which reaction results in the production of a labeled polyphosphate; b) permitting the labeled polyphosphate to react with a phosphatase to produce a detectable species; and c) detecting the presence of the detectable species.

Also provided is a method of detecting the presence of a nucleic acid sequence comprising the steps of: a) conducting a nucleic acid polymerase reaction in the presence of a manganese salt to increase the rate of utilization of a terminal-phosphate-labeled nucleoside polyphosphates and at least one terminal-phosphate-labeled nucleotide having four or more phosphate groups in the polyphosphate chain, which reaction results in the production of a labeled polyphosphate; and b) detecting the labeled polyphosphate.

In addition, the invention relates to a method of detecting the presence of a nucleic acid sequence comprising the steps of: a) conducting a nucleic acid polymerase reaction in the presence of a manganese salt to increase the rate of utilization of a terminal-phosphate-labeled nucleoside polyphosphates and at least one terminal-phosphate-labeled nucleotide having four or more phosphate groups in the polyphosphate chain, which reaction results in the production of a labeled polyphosphate; b) permitting the labeled polyphosphate to react with a phosphatase to produce a detectable species; and c) detecting the presence of the detectable species.

A further aspect of the present invention relates to a method of quantifying a nucleic acid including the steps of: a) conducting a nucleic acid polymerase reaction in the presence of a manganese salt to increase the rate of utilization of a terminal-phosphate-labeled nucleoside polyphosphates, wherein the reaction includes a terminal-phosphate-labeled nucleotide, which reaction results in production of labeled polyphosphate; b) permitting the labeled polyphosphate to react with a phosphatase to produce a detectable by-product species in an amount substantially proportional to the amount of nucleic acid; c) measuring the detectable species; and d) comparing the measurements using known standards to determine the quantity of nucleic acid.

The invention further relates to a method of quantifying a DNA sequence including the steps of: a) conducting a DNA polymerase reaction in the presence of a manganese salt to increase the rate of utilization of a terminal-phosphate-labeled nucleoside polyphosphates and a terminal-phosphate-labeled nucleotide, which reaction resulting in production of labeled polyphosphate; b) permitting the labeled polyphosphate to react with a phosphatase to produce a detectable by-product species in amounts substantially proportional to the amount of the DNA sequence; c) measuring the detectable species; and d) comparing the measurements using known standards to determine the quantity of DNA.

Another aspect of the invention relates to a method for determining the identity of a single nucleotide in a nucleic acid sequence, which includes the steps of: a) conducting a nucleic acid polymerase reaction in the presence of at least one terminal phosphate-labeled nucleotide and a manganese salt to increase the rate of utilization of a terminal-phosphate-labeled nucleoside polyphosphates, which reaction results in the production of labeled polyphosphate; b) permitting the labeled polyphosphate to react with a phosphatase to produce a detectable species; c) detecting the presence of the detectable species; and d) identifying the nucleoside incorporated.

Also provided is a method for determining the identify of a single nucleotide in a nucleic acid sequence including the following steps: a) conducting a nucleic acid polymerase reaction in the presence of a manganese salt to increase the rate of utilization of a terminal-phosphate-labeled nucleoside polyphosphates and at least one terminal-phosphate-labeled nucleotide having four or more phosphate groups in the polyphosphate chain, which reaction results in the production of labeled polyphosphate; b) permitting the labeled polyphosphate to react with a phosphatase to produce a detectable species; c) detecting the presence of said detectable species; and d) identifying the nucleoside incorporated.

The present invention further includes a nucleic acid detection kit wherein the kit includes:

a) at least one or more terminal-phosphate-labeled nucleotide according to the formula I:

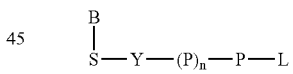

wherein P=phosphate ($PO_3$) and derivatives thereof, n is 2 or greater; Y is an oxygen or sulfur atom; B is a nitrogen-containing heterocyclic base; S is an acyclic moiety, carbocyclic moiety or sugar moiety; P-L is a phosphorylated label which becomes independently detectable when the phosphate is removed, wherein L is an enzyme-activatable label containing a hydroxyl group, a sulfhydryl group or an amino group suitable for forming a phosphate ester, a thioester, or a phosphoramidate linkage at the terminal phosphate of a natural or modified nucleotide;

b) at least one of DNA polymerase, RNA polymerase, or reverse transcriptase;

c) phosphatase; and d) reaction buffer containing a Manganese salt.

The present invention further includes a nucleic acid detection kit wherein the kit includes:

a) at least one or more terminal-phosphate-labeled nucleotide according to Formula I below:

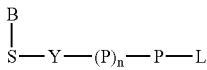

wherein P=phosphate (PO$_3$) and derivatives thereof, n is 2 or greater; Y is an oxygen or sulfur atom; B is a nitrogen-containing heterocyclic base; S is an acyclic moiety, carbocyclic moiety or sugar moiety; P-L is a phosphorylated label with a linker between L and P, wherein L is a label containing a hydroxyl group, a sulfhydryl group, a haloalkyl group or an amino group suitable for forming a phosphate ester, a thioester, an alkylphosphonate or a phosphoramidate linkage at the terminal phosphate of a natural or modified nucleotide;

b) at least one of DNA polymerase, RNA polymerase, or reverse transcriptase; and c) reaction buffer containing a Manganese salt.

Present invention also provides new terminal phosphate labeled nucleoside polyphosphates with linkers which are better substrates for polymerases. These nucleotides are represented by the structure below:

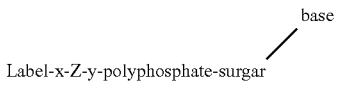

wherein Label is a detectable moiety, x and y are independently selected from CH$_2$, NH, O or S, Z is a linear, branched, cyclic, saturated or unsaturated hydrocarbon containing one or more heteroatoms and optionally containing positive or negative charges, polyphosphate is a tetraphosphate or higher phosphate, sugar is a natural or modified sugar and base is a natural or modified DNA or RNA base.

The present invention also provides manganese complexes of terminal phosphate labeled nucleoside polyphosphates of formula II:

wherein Label is a detectable moiety connected to NPP with or without a linker, NPP is a nucleoside polyphosphate with four or more phosphates, and x is 1 or more.

Further provided is a nucleic acid detection kit comprising:

a) at least one manganese complex of a terminal-phosphate labeled nucleoside polyphosphate of formula II:

wherein Label is a detectable moiety linked to NPP with or without a linker, NPP is a nucleoside polyphosphate with four or more phosphates, and x is 1 or more; and b) a nucleic acid polymerase.

Also provided is a nucleic acid detection kit comprising:

a) at least one manganese complex of a terminal-phosphate labeled nucleoside polyphosphate of formula II:

wherein Label is a detectable moiety linked to NPP with or without a linker, NPP is a nucleoside polyphosphate with four or more phosphates, and x is 1 or more;

b) a nucleic acid polymerase; and c) a metal-ion binding buffer

The objects and features of the invention are more fully apparent following review of the detailed description of the invention in conjunction with the accompanying drawings.

DETAILED DESCRIPTION OF THE PREFERRED EMBODIMENTS

Figure 1:
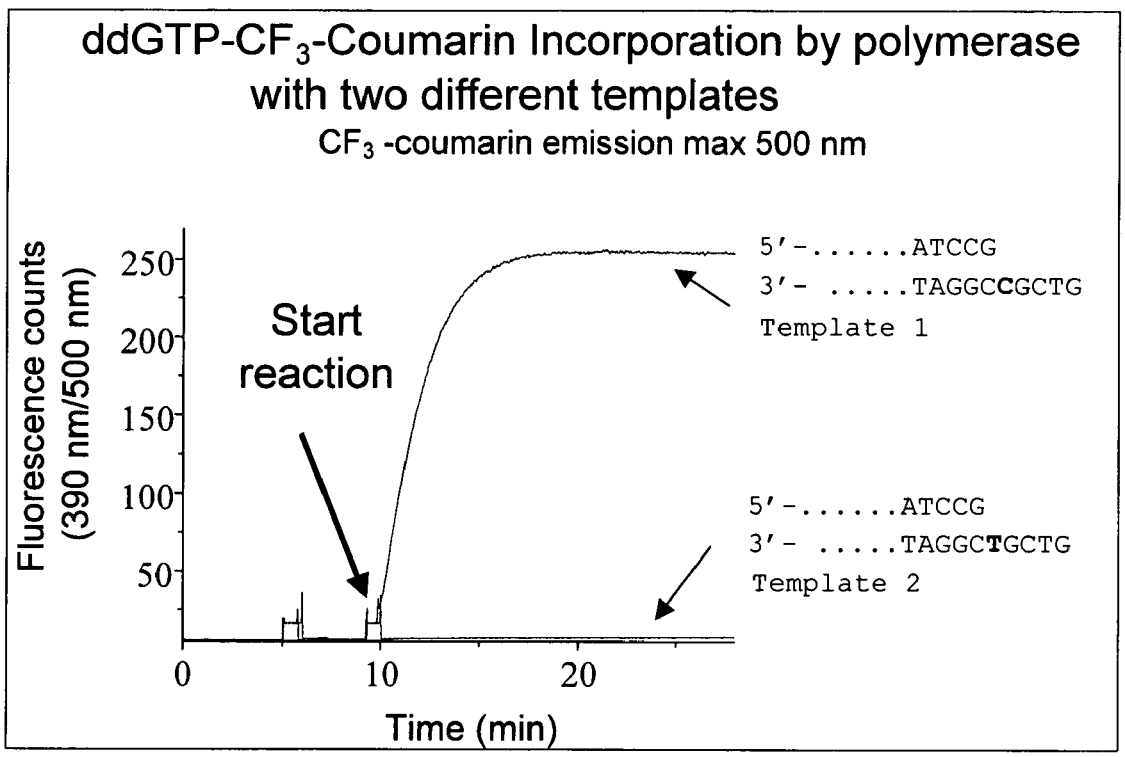
FIG. 1 is a graph showing fluorescence obtained by polymerase utilization of a gamma-phosphate-labeled ddGTP in a template-directed process in the presence of phosphatase.

The term "nucleoside" as defined herein is a compound including a purine deazapurine, pyrimidine or modified base linked to a sugar or a sugar substitute, such as a carbocyclic or acyclic moiety, at the 1' position or equivalent position and includes 2'-deoxy and 2'-hydroxyl, and 2',3'-dideoxy forms as well as other substitutions.

The term "nucleotide" as used herein refers to a phosphate ester of a nucleoside, wherein the esterification site typically corresponds to the hydroxyl group attached to the C-5 position of the pentose sugar.

The term "oligonucleotide" includes linear oligomers of nucleotides or derivatives thereof, including deoxyribonucleosides, ribonucleosides, and the like. Throughout the specification, whenever an oligonucleotide is represented by a sequence of letters, the nucleotides are in the 5'→3' order from left to right where A denotes deoxyadenosine, C denotes deoxycytidine, G denotes deoxyguanosine, and T denotes thymidine, unless noted otherwise.

The term "primer" refers to a linear oligonucleotide that anneals in a specific way to a unique nucleic acid sequence and allows for amplification of that unique sequence.

The phrase "target nucleic acid sequence" and the like refers to a nucleic acid whose sequence identity, or ordering or location of nucleosides is determined by one or more of the methods of the present invention The term "metal ion buffer" is meant a material which regulates the concentration of free metal ion, such as Mn$^{2+}$, in solution.

The present invention provides methods of using manganese salts in conjunction with terminal phosphate labeled nucleotides in enzymatic reactions to enhance their use by enzymes over and beyond what is observed in the absence of manganese even if other metal salts are present. A number of enzymes are known to use certain divalent metal ions as cofactors for their activity. In many cases these in a decrease in enzymatic activity. Inventors have discovered that with terminal-phosphate-labeled nucleoside polyphosphate, this is not true and addition of a different metal ion, in this case manganese actually increasing the rate of their utilization by enzymes that catalyze nucleoside monophosphate transfer.

Thus, the present invention provides a method of increasing the rate of an enzyme catalyzed nucleoside monophosphate transfer from a terminal-phosphate-labeled nucleoside polyphosphate to detect the activity of said enzyme or said terminal-phosphate-labeled nucleoside polyphosphate, said method comprising: Conducting said enzyme catalyzed nucleoside monophosphate transfer from a terminal-phosphate-labeled nucleoside polyphosphate reaction in reaction buffer comprising a manganese salt, thereby increasing the rate of said reaction over the rate of said reaction in the absence of manganese even if other divalent metal salts were present in the buffer.

The present invention relates to methods of detecting a polynucleotide in a sample wherein a convenient assay is used for monitoring RNA or DNA synthesis via nucleic acid polymerase activity. RNA and DNA polymerases synthesize oligonucleotides via transfer of a nucleoside monophosphate from a nucleoside triphosphate (NTP) or deoxynucleoside triphosphate (dNTP) to the 3' hydroxyl of a growing oligonucleotide chain. The force which drives this reaction is the cleavage of an anhydride bond and the con-commitant formation of an inorganic pyrophosphate. The present invention utilizes the finding that structural modification of the terminal-phosphate of the nucleotide does not abolish its ability to function in the polymerase reaction. The oligonucleotide synthesis reaction involves direct changes only at the α- and β-phosphoryl groups of the nucleotide, allowing nucleotides with modifications at the terminal phosphate position to be valuable as substrates for nucleic acid polymerase reactions. However, these terminal phosphate labeled nucleoside polyphosphates are very poor substrates for polymerases. The inventors have discovered that their substrate properties can be substantially enhanced by addition of a manganese salt.

Figure 3:
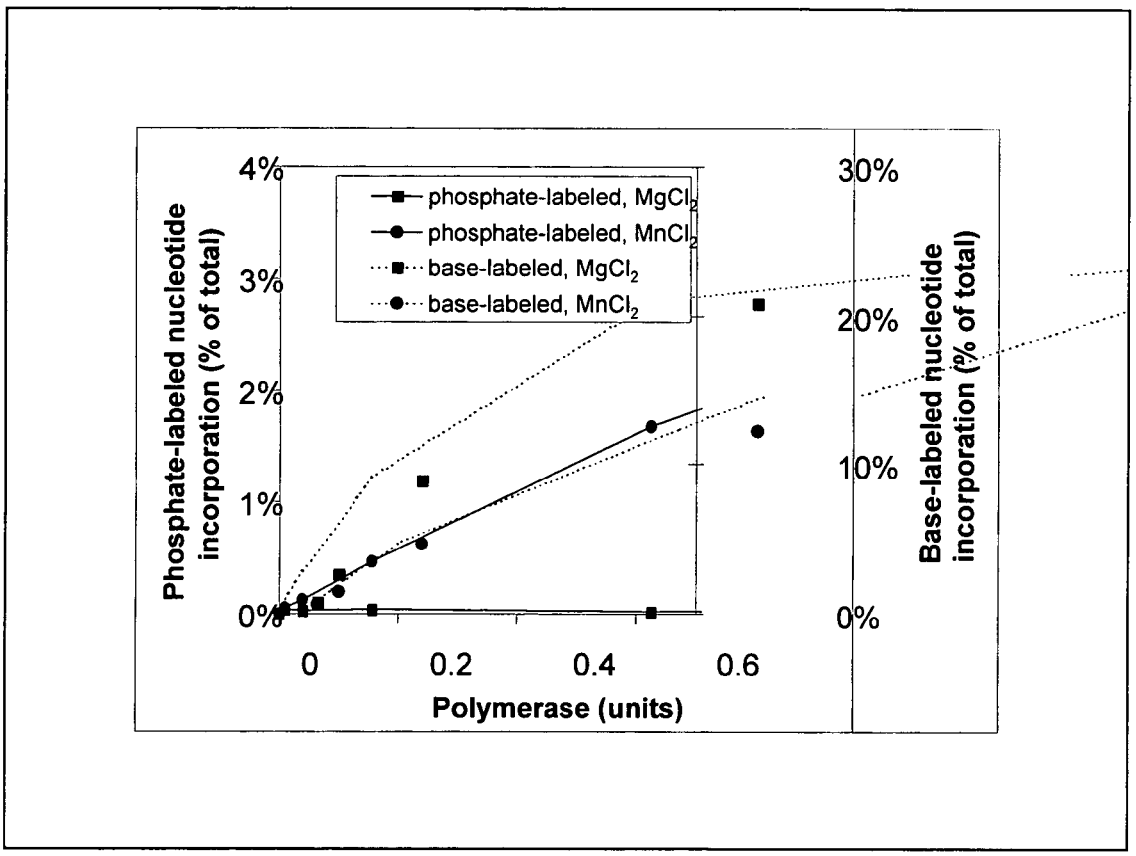
FIG. 3 is a graph showing the incorporation of base labeled dideoxynucleotides and phosphate-labeled-dideoxynucleotides in the presence of either Mg$^{++}$ or Mn$^{++}$ as cofactor.
Figure 4:
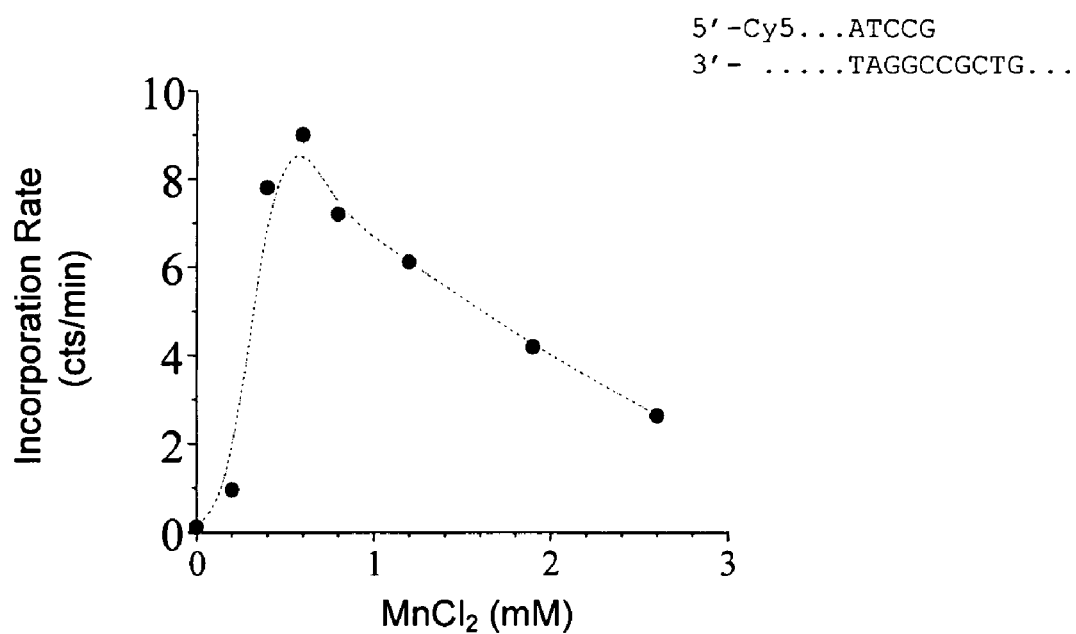
FIG. 4 is a graph showing the effect of MnCl$_2$ in the presence of fixed 5 mM MgCl$_2$ concentration on the incorporation of γ-rhodamine-6G labeled GTP using exonuclease deficient Phi 29 DNA polymerase.
Figure 6:
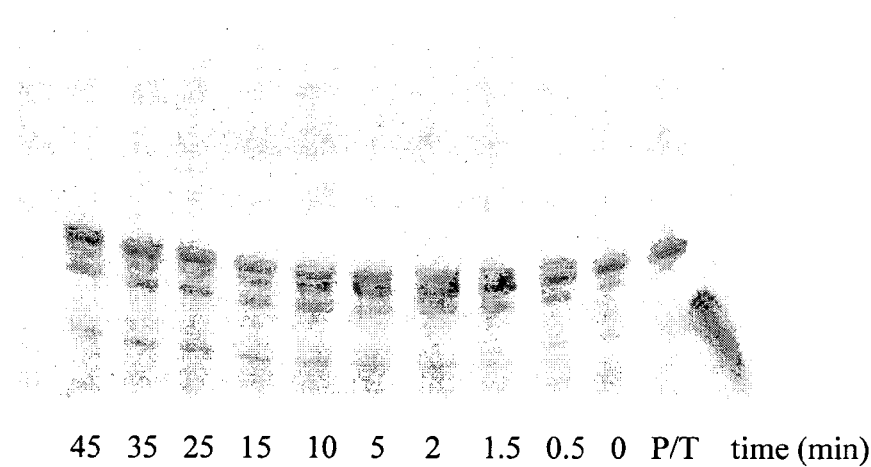
FIG. 6 is a graph showing the incorporation of dCTP-γ-ROX by exonuclease deficient Phi 29 DNA polymerase in the presence of only MnCl$_2$. No misincorporation was observed in the presence of Mn alone.
Figure 7A:
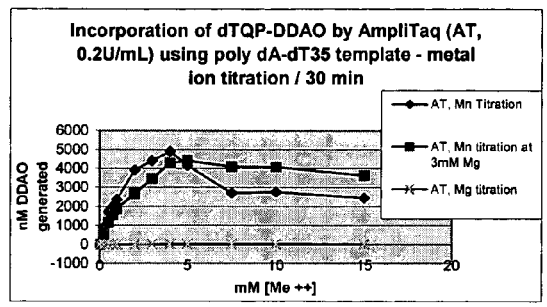
FIGS. 7A-7E, are a series of graphs showing the incorporation of a terminal-phosphate-labeled-ddT4P (ddT4P-DDAO) by different DNA polymerases on a poly A template in the presence of Mg$^{++}$ alone, Mn$^{++}$ alone and in presence of mixture of Mg$^{++}$ and Mn$^{++}$ salts.
Figure 7D:
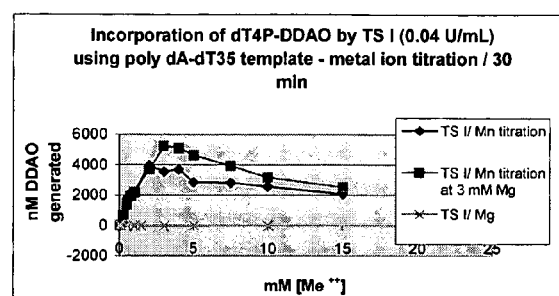
Figure 7B:
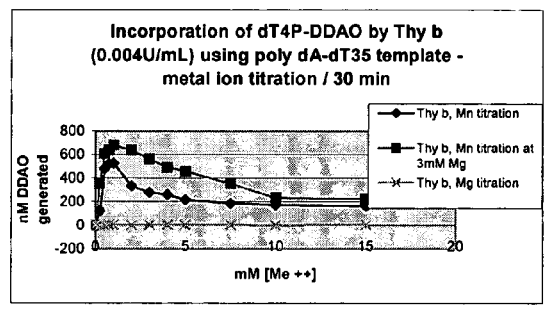
Figure 7E:
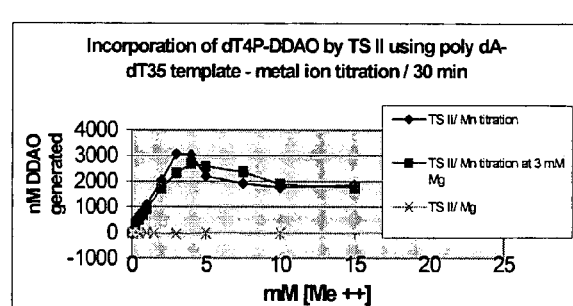
Figure 7C:
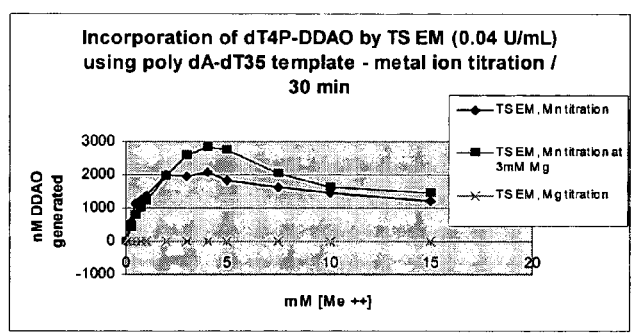

Thus the present invention provides a method of using terminal-phosphate-labeled nucleoside polyphosphates in the presence of a manganese salt, such presence resulting in the ability of terminal-phosphate-labeled nucleoside polyphosphates to act as better enzyme substrates. Manganese salts have been used in the past in sequencing methods (WO 99/37810) as well as in nucleic acid amplification methods. In the former case, the use of manganese was to attain uniformity in signal intensities due to sequencing fragments terminated with different bases, thereby simplifying the sequence analysis. But, as shown in FIG. 3, rate of incorporation of base labeled nucleotides in the presence of a manganese salt is actually lower than that in the presence of magnesium. In the case of nucleic acid amplification methods, the presence of manganese allowed amplification of longer DNA fragments, but in the process it also caused an increase in replication errors. The effect of manganese on polymerase utilization on terminal-phosphate-labeled nucleoside polyphosphates is quite different. As seen in FIG. 4, the addition of 0.05 mM $MnCl_2$ to a reaction mixture containing 5 mM $MgCl_2$ results in an increase in activity of more than 40-folds. Furthermore, there is no evidence that errors in incorporation are increased with $MnCl_2$ (FIG. 6). The amount of manganese required for this improvement in reaction rate can be as little as 10 μM and preferable concentrations range from 0.01 to 50 mM. More preferably, the concentration is between 0.05 to 10 mM. It has also been discovered that presence of other salts such as magnesium, sodium, potassium, calcium, etc., do not interfere with the effect of manganese on the substrate properties of terminal-phosphate labeled nucleoside polyphosphates.

In certain embodiments, the polymerase is a DNA polymerase, such as DNA polymerase I, II, or III or DNA polymerase α, β, γ, or terminal deoxynucleotidyl transferase or telomerase. In other embodiments, suitable polymerases include, but are not limited to, a DNA dependent RNA polymerase, a primase, or an RNA dependent DNA polymerase (reverse transcriptase).

The methods provided by this invention utilize a nucleoside polyphosphate, such as a deoxynucleoside polyphosphate, ribonucleoside polyphosphates, dideoxynucleoside polyphosphate, carbocyclic nucleoside polyphosphate, or acyclic nucleoside polyphosphate analogue with an electrochemical label, mass tag, or a calorimetric dye, chemiluminescent label, or a fluorescent label attached to the terminal-phosphate. When a nucleic acid polymerase uses this analogue as a substrate, an enzyme-activatable label would be present on the inorganic polyphosphate by-product of phosphoryl transfer. Cleavage of the polyphosphate product of phosphoryl transfer via phosphatase, leads to a detectable change in the label attached thereon. It is noted that while RNA and DNA polymerases are able to recognize nucleotides with modified terminal phosphoryl groups, the inventors have determined that this starting material is not a template for phosphatases. The scheme below shows the most relevant molecules in the methods of this invention; namely the terminal-phosphate-labeled nucleotide, the labeled polyphosphate by-product and the enzyme-activated label.

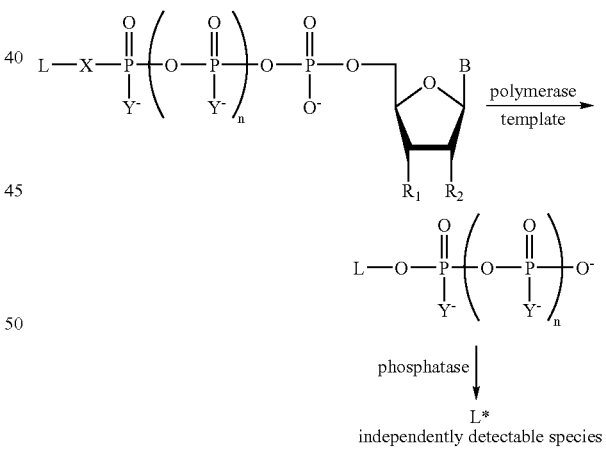

In the scheme above, n is 1 or greater, $R_1$ and $R_2$ are independently H, OH, SH, SR, OR, F, Br, Cl, I, $N_3$, NHR or $NH_2$; B is a nucleotide base or modified heterocyclic base; X is O, S, $CH_2$ or NH; Y is O, S, or $BH_3$; and L is a phosphatase activatable label with or without a linker which may be a colored or fluorescent dye, a chromogenic, fluorogenic or chemiluminescent molecule, a mass tag or an electrochemical tag. A mass tag is a small molecular weight moiety suitable for mass spectrometry that is readily distinguishable from other components due to a difference in mass. An electrochemical tag is an easily oxidizable or reducible species. It has been discovered that when n is 2 or greater, the nucleotides are significantly better substrates for polymerases than when n is 1. Therefore, in preferred embodiments, n is 2, 3 or 4, $R_1$ and $R_2$ are independently H or OH; X and Y are O; B is a nucleotide base and L is a label which may be a chromogenic, fluorogenic or a chemiluminescent molecule.

In one embodiment of the method of detecting the presence of a nucleic acid sequence provided herein, the steps include a) conducting a nucleic acid polymerase reaction in the presence of a Mn salt to increase the rate of utilization of a terminal-phosphate-labeled nucleoside polyphosphates, wherein the reaction includes a terminal-phosphate-labeled nucleotide and the said polymerase reaction results in the production of labeled polyphosphate; b) permitting the labeled polyphosphate to react with a phosphatase suitable to hydrolyze the phosphate ester and to produce a detectable species; and c) detecting the presence of a detectable species by suitable means. In this embodiment, the template used for the nucleic acid polymerase reaction may be a heteropolymeric or homopolymeric template. By terminal-phosphate-labeled nucleotide, it is meant throughout the specification that the labeled polyphosphate con-committantly released following incorporation of the nucleoside monophosphate into the growing nucleotide chain, may be detected as such with or without separation or may be reacted with the phosphatase to produce a detectable species. Other nucleotides may be included in the reaction which are substantially non-reactive to phosphatase, for example, nucleotides blocked at the terminal-phosphate by a moiety which does not lead to the production of a detectable species. The nucleic acid for detection in this particular embodiment may include RNA, a natural or synthetic oligonucleotide, mitochondrial or chromosomal DNA.

The invention further provides a method of detecting the presence of a DNA sequence including the steps of a) conducting a DNA polymerase reaction in the presence of a Mn salt and terminal-phosphate labeled nucleotide, which reaction results in the production of a labeled polyphosphate; b) permitting the labeled polyphosphate to react with a phosphatase to produce a detectable species; and c) detecting the presence of said detectable species. The DNA sequence for detection may include DNA isolated from cells, chemically treated DNA such as bisulfite treated methylated DNA or DNA chemically or enzymatically synthesized according to methods known in the art. Such methods include PCR, and those described in DNA Structure Part A: Synthesis and Physical analysis of DNA, Lilley, D. M. J. and Dahlberg, J. E. (Eds.), Methods Enzymol., 211, Academic Press, Inc., New York (1992), which is herein incorporated by reference. The DNA sequence may further include chromosomal DNA and natural or synthetic oligonucleotides. The DNA may be either double- or single-stranded.

The methods of the invention may further include the step of including one or more additional detection reagents in the polymerase reaction. The additional detection reagent may be capable of a response that is detectably different from the detectable species. For example, the additional detection reagent may be an antibody.

Suitable nucleotides for addition as substrates in the polymerase reaction include nucleoside polyphosphates, such as including, but not limited to, deoxyribonucleoside polyphosphates, ribonucleoside polyphosphates, dideoxynucleoside polyphosphates, carbocyclic nucleoside polyphosphates and acyclic nucleoside polyphosphates and analogs thereof. Particularly desired are nucleotides containing 3, 4, 5 or 6 phosphate groups in the polyphosphate chain, where the terminal phosphate is labeled.

It is noted that in embodiments including terminal-phosphate-labeled nucleotides having four or more phosphates in the polyphosphate chain, it is within the contemplation of the present invention that the labeled polyphosphate by-product of phosphoryl transfer may be detected without the use of phosphatase treatment. For example, it is known that natural or modified nucleoside bases, particularly guanine, can cause quenching of fluorescent markers. Therefore, in a terminal-phosphate-labeled nucleotide, the label may be partially quenched by the base. Upon incorporation of the nucleoside monophosphate, the label polyphosphate by-product may be detected due to its enhanced fluorescence. Alternatively, it is possible to physically separate the labeled polyphosphate product by chromatographic separation methods before identification by fluorescence, color, chemiluminescence, or electrochemical detection. In addition, mass spectrometry could be used to detect the products by mass difference.

The methods of the present invention may include conducting the polymerase reaction in the presence of at least one of DNA or RNA polymerase. Suitable nucleic acid polymerases may also include primases, telomerases, terminal deoxynucleotidyl transferases, and reverse transcriptases. A nucleic acid template may be required for the polymerase reaction to take place and may be added to the polymerase reaction solution. It is anticipated that all of the steps a), b) and c) in the detection methods of the present invention could be run concurrently using a single, homogenous reaction mixture, as well as run sequentially.

It is well within the contemplation of the present invention that nucleic acid polymerase reactions may include amplification methods that utilize polymerases. Examples of such methods include polymerase chain reaction (PCR), rolling circle amplification (RCA), and nucleic acid sequence based amplification (NASBA). For e.g., wherein the target molecule is a nucleic acid polymer such as DNA, it may be detected by PCR incorporation of a gamma-phosphate labeled nucleotide base such as adenine, thymine, cytosine, guanine or other nitrogen heterocyclic bases into the DNA molecule. The polymerase chain reaction (PCR) method is described by Saiki et al in Science Vol. 239, page 487, 1988, Mullis et al in U.S. Pat. No. 4,683,195 and by Sambrook, J. et al. (Eds.), Molecular Cloning, second edition, Cold Spring Harbor Laboratory Press, Cold Spring Harbor, N.Y. (1980), Ausubel, F. M. et al. (Eds.), Current Protocols in Molecular Biology, John Wiley & Sons, Inc., NY (1999), and Wu, R. (Ed.), Recombinant DNA Methodology II, Methods in Zumulogy, Academic Press, Inc., NY, (1995). Using PCR, the target nucleic acid for detection such as DNA is amplified by placing it directly into a reaction vessel containing the PCR reagents and appropriate primers. Typically, a primer is selected which is complimentary in sequence to at least a portion of the target nucleic acid.

It is noted that nucleic acid polymerase reactions suitable for conducting step a) of the methods of the present invention may further include various RCA methods of amplifying nucleic acid sequences. For example, those disclosed in U.S. Pat. No. 5,854,033 to Lizardi, Paul M., incorporated herein by reference, are useful. Polymerase reactions may further include the nucleic acid sequence based amplification (NASBA) wherein the system involves amplification of RNA, not DNA, and the amplification is iso-thermal, taking place at one temperature (41° C.). Amplification of target RNA by NASBA involves the coordinated activities of three enzymes: reverse transcriptase, Rnase H, and T7 RNA polymerase along with oligonucleotide primers directed toward the sample target RNA. These enzymes catalyze the exponential amplification of a target single-stranded RNA in four steps: extension, degradation, DNA synthesis and cyclic RNA amplification.

Methods of RT-PCR, RCA, and NASBA generally require that the original amount of target nucleic acid is indirectly measured by quantification of the amplification products. Amplification products are typically first separated from starting materials via electrophoresis on an agarose gel to confirm a successful amplification and are then quantified using any of the conventional detection systems for a nucleic acid such as detection of fluorescent labels, enzyme-linked detection systems, antibody-mediated label detection and detection of radioactive labels. In contrast, the present method eliminates the need to separate products of the polymerase reaction from starting materials before being able to detect these products. For example, in the present invention, a reporter molecule (fluorescent, chemiluminescent or a chromophore) or other useful molecule is attached to the nucleotide in such a way that it is undetectable under certain conditions when masked by the phosphate attachment. However, following the incorporation of the nucleotide into the growing oligonucleotide chain and phosphatase treatment of the reaction, the label is detectable under those conditions. For example, if the hydroxyl group on the side of the triple ring structure of 1,3-dichloro-9,9-dimethyl-acridine-2-one (DDAO) is attached to the terminal-phosphate position of the nucleotide, the DDAO does not fluoresce at 659 nm. Once the nucleoside monophosphate is incorporated into DNA, the other product, DDAO polyphosphate (which also does not fluoresce at 659 nm) is a substrate for phosphatase. Once de-phosphorylated to form DDAO, the dye moiety will become fluorescent at 659 nm and hence detectable. The specific analysis of the polyphosphate product can be carried out in the polymerase reaction solution, eliminating the need to separate reaction products from starting materials. This scheme allows for the detection and, optionally, quantitation of nucleic acids formed during polymerase reactions using routine instrumentation such as spectrophotometers.

In the methods described above, the polymerase reaction step may further include conducting the polymerase reaction in the presence of a phosphatase, which converts labeled polyphosphate by-product to the detectable label. As such, a convenient assay is established for detecting the presence of a nucleic acid sequence that allows for continuous monitoring of detectable species formation. This represents a homogeneous assay format in that it can be performed in a single tube.

One format of the assay methods described above may include, but is not limited to, conducting the polymerase reaction in the presence of a single type of terminal-phosphate-labeled nucleotide capable of producing a detectable species. For example, terminal-phosphate-modified ATP, wherein all other nucleotides are substantially non-reactive to phosphatase, but yield non-detectable species.

In another assay format, the polymerase reaction may be conducted in the presence of more than one type of terminal-phosphate-labeled nucleotide, each type capable of producing a uniquely detectable species. For example, the assay may include a first nucleotide (e.g., adenosine polyphosphate) that is associated with a first label which when liberated enzymatically from the inorganic polyphosphate by-product of phosphoryl transfer, emits light at a first wavelength and a second nucleotide (e.g., guanosine polyphosphate) associated with a second label that emits light at a second wavelength. Desirably, the first and second wavelength emissions have substantially little or no overlap. It is within the contemplation of the present invention that multiple simultaneous assays based on nucleotide sequence information can thereafter be derived based on the particular label released from the polyphosphate.

Another aspect of present invention provides metal-ion buffers that regulate the concentration of manganese ions in the reaction medium. A buffer regulates the concentration of a species (e.g., a metal ion) in solution by resisting changes in the concentration of the free ion in response to dilutions or to additions or substraction of that ion from the solution. Such a buffer can, for example, be a carboxylic acid, e.g., an alkyl-dicarboxylic acid such as tartaric acid, where alkyl is straight or branched chain of 1-8 carbon atoms. Other examples of dicarboxylic acid include oxalic acid, malonic acid, succinic acid, maleic acid, glutaric acid, adipic acid, fumaric acid, glutamic acid, aspartic acid, and phthalic acid. Other metal ion buffer include, for example, citric acid, N-hydroxyethyliminodiacetic acid, 2-(N-morpholino)ethanesulphonic acid, dithiothreitol, and N,N-bishydroxyrthylglysine. A metal ion buffer may be used in the presence of a pH buffer (i.e, a compound which regulates the concentration of free $H^+$ in solution). The manganese ion will normally come from a salt, for example, manganese sulphate ($MnSO_4$), manganese chloride ($MnCl_2$), or manganese acetate.

By "dicarboxylic acid" is meant any lower alkyl, hydroxyalkyl, or aminoalkyl compound containing two carboxylic acid groups, such as oxalic acid, malonic acid, succinic acid, maleic acid, tartaric acid, glutamic acid, adipic acid, fumaric acid, phthalic acid, glutaric acid, or aspartic acid.

The methods described above may further include the step of quantifying the nucleic acid sequence. In a related aspect, the detectable species may be produced in amounts substantially proportional to the amount of an amplified nucleic acid sequence. The step of quantifying the nucleic acid sequence is desired to be done by comparison of spectra produced by the detectable species with known spectra.

In one embodiment, the invention provides a method of quantifying a nucleic acid including the steps of: a) conducting a nucleic acid polymerase reaction in the presence of a manganese salt, the polymerase reaction including the reaction of a nucleotide which is substantially non-reactive to phosphatase in addition to at least one terminal-phosphate-labeled nucleotide, wherein the reaction results in the production of labeled polyphosphate; b) permitting the labeled polyphosphate to react with a phosphatase to produce a detectable by-product species in an amount substantially proportional to the amount of the nucleic acid to be quantified; c) measuring the detectable species; and d) comparing the measurements using known standards to determine the quantity of the nucleic acid. In this embodiment of the method of quantifying a nucleic acid, the nucleic acid to be quantified may be RNA. The nucleic acid may further be a natural or synthetic oligonucleotide, chromosomal DNA, or DNA.

The invention further provides a method of quantifying a DNA sequence including the steps of: a) conducting a DNA polymerase reaction in the presence of a manganese salt to increase the rate of utilization of a terminal-phosphate-labeled nucleoside polyphosphates and a terminal-phosphate-labeled nucleotide wherein the reaction results in the production of labeled polyphosphate; b) permitting the labeled polyphosphate to react with a phosphatase to produce a detectable by-product species in amounts substantially proportional to the amount of the DNA sequence to be quantified; c) measuring the detectable species; and d) comparing measurements using known standards to determine the quantity of DNA. In this embodiment, the DNA sequence for quantification may include natural or synthetic oligonucleotides, or DNA isolated from cells including chromosomal DNA.

In each of these methods of quantifying a nucleic acid sequence described above, the polymerase reaction step may further include conducting the polymerase reaction in the presence of a phosphatase. As described earlier in the specification, this would permit real-time monitoring of nucleic acid polymerase activity and hence, real-time detection of a target nucleic acid sequence for quantification.

The terminal-phosphate-labeled nucleotide useful for the methods of quantifying the nucleic acid sequence provided herein may be represented by the Formula I shown above. The most useful examples include those with enzyme-activatable label. This enzyme-activatable label becomes detectable through the enzymatic activity of phosphatase which changes the phosphate ester linkage between the label and the terminal-phosphate of a natural or modified nucleotide in such a way to produce a detectable species. The detectable species is detectable by the presence of any one of or a combination of color, fluorescence emission, chemiluminescence, mass difference or electrochemical potential. As already described above, the enzyme-activatable label may be a 1,2-dioxetane chemiluminescent compound, fluorescent dye, chromogenic dye, a mass tag or an electrochemical tag or a combination thereof. Suitable labels are the same as those described above.

As will be described in further detail in the Example Section, the present invention provides methods for determining the identity of a single nucleotide in a target nucleic acid sequence. These methods include the steps of: a) conducting a nucleic acid polymerase reaction in the presence of a manganese salt to increase the rate of utilization of a terminal-phosphate-labeled nucleoside polyphosphates and at least one terminal phosphate-labeled nucleotide, which reaction results in the production of labeled polyphosphate; b) permitting the labeled polyphosphate to react with a phosphatase to produce a detectable species; c) detecting the presence of the detectable species; and d) identifying the nucleoside incorporated. In desired embodiments, the terminal phosphate-labeled nucleotide includes four or more phosphates in the polyphosphate chain.

In one aspect of the methods of detecting the presence of a nucleic acid sequence described above, the terminal-phosphate-labeled nucleotide may be represented by the Formula I:

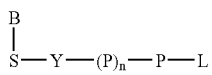

wherein P=phosphate (PO$_3$) and derivatives thereof, n is 2 or greater; Y is an oxygen or sulfur atom; B is a nitrogen-containing heterocyclic base; S is an acyclic moiety, carbocyclic moiety or sugar moiety; P-L is a phosphorylated label which becomes independently detectable when the phosphate is removed, wherein L is an enzyme-activatable label containing a hydroxyl group, a sulfhydryl group or an amino group suitable for forming a phosphate ester, a thioester, or a phosphoramidate linkage at the terminal phosphate of a natural or modified nucleotide.

In another aspect of the methods of detecting the presence of a nucleic acid sequence described above, the terminal-phosphate-labeled nucleotide may be represented by the Formula I:

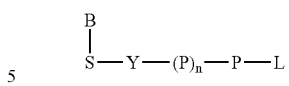

wherein P=phosphate (PO$_3$) and derivatives thereof, n is 2 or greater; Y is an oxygen or sulfur atom; B is a nitrogen-containing heterocyclic base; S is an acyclic moiety, carbocyclic moiety or sugar moiety; P-L is a phosphorylated label with—a linker between L and P, wherein L is a label containing a hydroxyl group, a sulfhydryl group, a haloalkyl group or an amino group suitable for forming a phosphate ester, a thioester, an alkylphosphonate or a phosphoramidate linkage at the terminal phosphate of a natural or modified nucleotide.

Another embodiment of current invention provides new terminal phosphate labeled nucleotides with linkers connecting the nucleoside polyphosphate (tetra-, penta-, hexa-) to the label used in the current invention to make them better substrates for polymerase. These compounds are represented by the formula

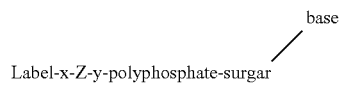

wherein Label is a detectable moiety, x and y are independently selected from CH$_2$, NH, O, and S: Z is a linear, branched, cyclic, saturated or unsaturated hydrocarbon containing one or more heteroatoms and optionally containing positive or negative charges; polyphosphate is a tetraphosphate or higher phosphate; sugar is a natural or modified sugar; and base is a natural or modified DNA or RNA base.

In preferred embodiments of the current invention the linker, x-Z-y contains 3-100 atoms and may contain positive or negative charges. In more preferred embodiments, the linker, x-Z-y is selected from alkane diols, diamines, aminoalcohols, dimercaptans, aminoacids, peptides, aminomercaptans and combinations thereof.

The present invention also describes manganese complexes of terminal-phosphate-labeled nucleoside polyphosphates of formula II:

wherein Label is a detectable moiety connected to NPP with or without a linker, NPP is a nucleoside polyphosphate with four or more phosphates, and x is 1 or more.

These complexes are simply generated by mixing the terminal-phosphate-labeled nucleoside polyphosphates with manganese salts and depending upon the number of phosphates in the polyphosphate chain the number of manganese ions complexed to the nucleotide can vary. In preferred compositions, the reactive terminal-phosphate labeled nucleoside polyphosphate has at least one manganese ion.

For purposes of the methods and new compositions of the present invention, useful carbocyclic moieties have been described by Ferraro, M. and Gotor, V. in Chem Rev. 2000, volume 100, 4319-48. Suitable sugar moieties are described by Joeng, L. S. et al., in J. Med. Chem. 1993, vol. 356, 2627-38; by Kim H. O. et al., in J. Med. Chem. 193, vol. 36, 30-7; and by Eschenmosser A., in Science 1999, vol. 284, 2118-2124. Moreover, useful acyclic moieties have been described by Martinez, C. I., et al., in Nucleic Acids Research 1999, vol. 27, 1271-1274; by Martinez, C. I., et al., in Bioorganic & Medicinal Chemistry Letters 1997, vol. 7, 3013-3016; and in U.S. Pat. No. 5,558,91 to Trainer, G. L. Structures for these moieties are shown below, where for all moieties R may be H, OH, NHR, F, N₃, SH, SR, OR lower alkyl and aryl; for the sugar moieties X and Y are independently O, S, or NH; and for the acyclic moieties, X=O, S, NH, NR.

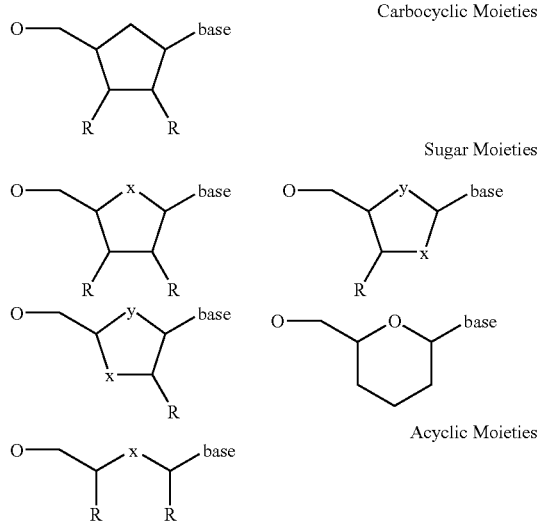

Carbocyclic Moieties

Sugar Moieties

Acyclic Moieties

In certain embodiments, the sugar moiety in formula may be selected from the following: ribosyl, 2'-deoxyribosyl, 3'-deoxyribosyl, 2',3'-didehydrodideoxyribosyl, 2',3'-dideoxyribosyl, 2'- or 3'-alkoxyribosyl, 2'- or 3'-aminoribosyl, 2'- or 3'-fluororibosyl, 2'- or 3'-mercaptoribosyl, 2'- or 3'-alkylthioribosyl, acyclic, carbocyclic and other modified sugars.

Moreover, in the above formula, the base may include uracil, thymine, cytosine, 5-methylcytosine, guanine, 7-deazaguanine, hypoxanthine, 7-deazahypoxanthine, adenine, 7-deazaadenine, 2,6-diaminopurine or analogs thereof.

The label attached at the terminal-phosphate position in the terminal-phosphate-labeled nucleotide may be selected from the group consisting of 1,2-dioxetane chemiluminescent compounds, fluorogenic dyes, chromogenic dyes, mass tags and electrochemical tags. This would allow the detectable species to be detectable by the presence of any one of color, fluorescence emission, chemiluminescence, mass change, electrochemical detection or a combination thereof.

Examples of labels that may be attached to the terminal phosphate group either directly or through linkers are give in Tables 1-2 below and some examples of terminal phosphate labeled nucleoside polyphosphates with directly attached labels that become detectable after removal of phosphate as well as terminal phosphate labeled nucleotides with labels that are detectable without the removal of phosphates are shown in Tables 3 & 4 respectively.

TABLE 1

Examples of detectable label moieties that become independently detectable after removal of phosphate residues

| | |
|---|---|
| 9H-(1,3-dichloro-9,9-dimethyl-7-hydroxyacridin-2-one) | 9H-(9,9-dimethyl-7-hydroxyacridin-2-one) |
| 9H-(1,3-dibromo-9,9-dimethyl-7-hydroxyacridin-2-one) | Resorufin |

TABLE 1-continued

Examples of detectable label moieties that become independently detectable after removal of phosphate residues

| | |
|---|---|
| Umbelliferone (7-hydroxycoumarin) | 4-Methylumbelliferone |
| 4-Trifluoromethylumbelliferone | 3-Cyanoumbelliferone |
| 3-Phenylumbelliferone | 3,4-Dimethylumbelliferone |
| 3-Acetylumbelliferone | 6-Methoxyumbelliferone |
| SNAFL ™ | Fluorescein ethyl ether |
| Naphthofluorescein | Naphthofluorescein ethyl ether |
| SNARF ™ | Rhodol green ™ |
| meso-Hydroxymonocarbocyanine | meso-hydroxytricarbocyanine |
| meso-hydroxydicarbocyanine | bis-(1,3-dibutylbarbituricacid) pentamethineoxonol |
| 1-Ethyl-2-(naphthyl-1-vinylene)-3,3-dimethyl-indolinium salt | |
| 2-Hydroxy-5'-chloro-phenyl-4-(3H)-6-chloro-quinazolone | |
| Trifluoroacetyl-R110 | Acetyl-R110 |
| 8-Hydroxy-2H-dibenz(b,f)azepin-2-one | 8-hydroxy-11,11-dimethyl-11H-dibenz(b,e)(1,4)oxazepin-2-one |
| 2-hydroxy-11,11-dimethyl-11H-dibenz(b,e)(1,4)oxazepin-8-one | Hydroxypyrene |

TABLE 2

Examples of detectable moieties that are detectable even when attached to the nucleoside polyphosphate

| | |
|---|---|
| Rhodamine green carboxylic acid | Carboxy-fluorescein |
| Pyrene | Dansyl |
| Bodipy | Dimethylamino-coumarin carboxylic acid |
| Eosin-5-isothiocyanate | Methoxycoumarin carboxylic acid |
| Texas Red | Oregon Green ™ 488 carboxylic acid |
| Rhodamine 110 | Rhodamine6G |
| Alexa ™ Dyes | |
| ROX | TAMRA |
| Anthracene-isothiocyanate | Cy ™ 3 |
| Cy ™ 3.5 | Cy ™ 5 |
| Cy ™ 5.5 | Cy ™ 7 |
| Anilinonaphthalene-sulfonic acid | |

In addition energy transfer dyes made by conjugating a donor dye and an acceptor dye are also useful in the current invention.

TABLE 3

Some examples of Labeled Nucleoside Polyphosphates where label is directly attached to the polyphosphate chain Adenosine-5'-(δ-7-(9H-(1,3-dichloro-9,9-dimethylacridin-2-one)))triphosphate or A3P-DDAO
Guanosine-5'-(δ-7-(9H-(1,3-dichloro-9,9-dimethylacridin-2-one)))triphosphate or G3P-DDAO
Cytidine-5'-(δ-7-(9H-(1,3-dichloro-9,9-dimethylacridin-2-one)))triphosphate or C3P-DDAO
Thymidine-5'-(δ-7-(9H-(1,3-dichloro-9,9-dimethylacridin-2-one)))triphosphate or T3P-DDAO
Uridine-5'-(δ-7-(9H-(1,3-dichloro-9,9-dimethylacridin-2-one)))triphosphate or U3P-DDAO
2'-Deoxyadenosine-5'-(δ-7-(9H-(1,3-dichloro-9,9-dimethylacridin-2-one)))triphosphate or dA3P-DDAO
2'-Deoxyguanosine-5'-(δ-7-(9H-(1,3-dichloro-9,9-dimethylacridin-2-one)))triphosphate or dG3P-DDAO
2'-Deoxycytidine-5'-(δ-7-(9H-(1,3-dichloro-9,9-dimethylacridin-2-one)))triphosphate or dC3P-DDAO
2'-Deoxythymidine-5'-(δ-7-(9H-(1,3-dichloro-9,9-dimethylacridin-2-one)))triphosphate or dT3P-DDAO TABLE 3-continued Some examples of Labeled Nucleoside Polyphosphates where
label is directly attached to the polyphosphate chain 2'-Deoxyuridine-5'-(δ-7-(9H-(1,3-dichloro-9,9-dimethylacridin-2-
one)))triphosphate or dU3P-DDAO
2',3'-Dideoxyadenosine-5'-(δ-7-(9H-(1,3-dichloro-9,9-dimethylacridin-2-
one)))triphosphate or ddA3P-DDAO
2',3'-Dideoxyguanosine-5'-(δ-7-(9H-(1,3-dichloro-9,9-dimethylacridin-2-
one)))triphosphate or ddG3P-DDAO
2',3'-Dideoxycytidine-5'-(δ-7-(9H-(1,3-dichloro-9,9-dimethylacridin-2-
one)))triphosphate or ddC3P-DDAO
2',3'-Dideoxythymidine-5'-(δ-7-(9H-(1,3-dichloro-9,9-dimethylacridin-2-
one)))triphosphate or ddT3P-DDAO
2',3'-Dideoxyuridine-5'-(δ-7-(9H-(1,3-dichloro-9,9-dimethylacridin-2-
one)))triphosphate or ddU3P-DDAO
3'-Deoxyadenosine-5'-(δ-7-(9H-(1,3-dichloro-9,9-dimethylacridin-2-
one)))triphosphate or 3'-dA3P-DDAO
3'-Deoxyguanosine-5'-(δ-7-(9H-(1,3-dichloro-9,9-dimethylacridin-2-
one)))triphosphate or 3'-dG3P-DDAO
3'-Deoxycytidine-5'-(δ-7-(9H-(1,3-dichloro-9,9-dimethylacridin-2-
one)))triphosphate or 3'-dC3P-DDAO
3'-Deoxythymidine-5'-(δ-7-(9H-(1,3-dichloro-9,9-dimethylacridin-2-
one)))triphosphate or 3'-dT3P-DDAO
3'-Deoxyuridine-5'-(δ-7-(9H-(1,3-dichloro-9,9-dimethylacridin-2-
one)))triphosphate or 3'-dU3P-DDAO
Adenosine-5'-(δ-7-(9H-(1,3-dichloro-9,9-dimethylacridin-2-
one)))tetraphosphate or A4P-DDAO
Guanosine-5'-(δ-7-(9H-(1,3-dichloro-9,9-dimethylacridin-2-
one)))tetraphosphate or G4P-DDAO
Cytidine-5'-(δ-7-(9H-(1,3-dichloro-9,9-dimethylacridin-2-
one)))tetraphosphate or C4P-DDAO
Thymidine-5'-(δ-7-(9H-(1,3-dichloro-9,9-dimethylacridin-2-
one)))tetraphosphate or T4P-DDAO
Uridine-5'-(δ-7-(9H-(1,3-dichloro-9,9-dimethylacridin-2-
one)))tetraphosphate or U4P-DDAO
2'-Deoxyadenosine-5'-(δ-7-(9H-(1,3-dichloro-9,9-dimethylacridin-2-
one)))tetraphosphate or dA4P-DDAO
2'-Deoxyguanosine-5'-(δ-7-(9H-(1,3-dichloro-9,9-dimethylacridin-2-
one)))tetraphosphate or dG4P-DDAO
2'-Deoxycytidine-5'-(δ-7-(9H-(1,3-dichloro-9,9-dimethylacridin-2-
one)))tetraphosphate or dC4P-DDAO
2'-Deoxythymidine-5'-(δ-7-(9H-(1,3-dichloro-9,9-dimethylacridin-2-
one)))tetraphosphate or dT4P-DDAO
2'-Deoxyuridine-5'-(δ-7-(9H-(1,3-dichloro-9,9-dimethylacridin-2-
one)))tetraphosphate or dU4P-DDAO
2',3'-Dideoxyadenosine-5'-(δ-7-(9H-(1,3-dichloro-9,9-dimethylacridin-2-
one)))tetraphosphate or ddA4P-DDAO
2',3'-Dideoxyguanosine-5'-(δ-7-(9H-(1,3-dichloro-9,9-dimethylacridin-2-
one)))tetraphosphate or ddG4P-DDAO
2',3'-Dideoxycytidine-5'-(δ-7-(9H-(1,3-dichloro-9,9-dimethylacridin-2-
one)))tetraphosphate or ddC4P-DDAO
2',3'-Dideoxythymidine-5'-(δ-7-(9H-(1,3-dichloro-9,9-dimethylacridin-2-
one)))tetraphosphate or ddT4P-DDAO
2',3'-Dideoxyuridine-5'-(δ-7-(9H-(1,3-dichloro-9,9-dimethylacridin-2-
one)))tetraphosphate or ddU4P-DDAO
3'-Deoxyadenosine-5'-(δ-7-(9H-(1,3-dichloro-9,9-dimethylacridin-2-
one)))tetraphosphate or 3'-dA4P-DDAO
3'-Deoxyguanosine-5'-(δ-7-(9H-(1,3-dichloro-9,9-dimethylacridin-2-
one)))tetraphosphate or 3'-dG4P-DDAO
3'-Deoxycytidine-5'-(δ-7-(9H-(1,3-dichloro-9,9-dimethylacridin-2-
one)))tetraphosphate or 3'-dC4P-DDAO
3'-Deoxythymidine-5'-(δ-7-(9H-(1,3-dichloro-9,9-dimethylacridin-2-
one)))tetraphosphate or 3'-dT4P-DDAO
3'-Deoxyuridine-5'-(δ-7-(9H-(1,3-dichloro-9,9-dimethylacridin-2-
one)))tetraphosphate or 3'-dU4P-DDAO
Adenosine-5'-(ε-7-(9H-(1,3-dichloro-9,9-dimethylacridin-2-
one)))pentaphosphate or A5P-DDAO
Guanosine-5'-(ε-7-(9H-(1,3-dichloro-9,9-dimethylacridin-2-
one)))pentaphosphate or G5P-DDAO
Cytidine-5'-(ε-7-(9H-(1,3-dichloro-9,9-dimethylacridin-2-
one))) pentaphosphate or C5P-DDAO
Thymidine-5'-(ε-7-(9H-(1,3-dichloro-9,9-dimethylacridin-2-
one)))pentaphosphate or T5P-DDAO
Uridine-5'-(ε-7-(9H-(1,3-dichloro-9,9-dimethylacridin-2-
one)))pentaphosphate or U5P-DDAO
2'-Deoxyadenosine-5'-(ε-7-(9H-(1,3-dichloro-9,9-dimethylacridin-2-
one)))pentaphosphate or dA5P-DDAO
2'-Deoxyguanosine-5'-(ε-7-(9H-(1,3-dichloro-9,9-dimethylacridin-2-
one)))pentaphosphate or dG5P-DDAO TABLE 3-continued Some examples of Labeled Nucleoside Polyphosphates where
label is directly attached to the polyphosphate chain 2'-Deoxycytidine-5'-(ε-7-(9H-(1,3-dichloro-9,9-dimethylacridin-2-
one)))pentaphosphate or dC5P-DDAO
2'-Deoxythymidine-5'-(ε-7-(9H-(1,3-dichloro-9,9-dimethylacridin-2-
one)))pentaphosphate or dT5P-DDAO
2'-Deoxyuridine-5'-(ε-7-(9H-(1,3-dichloro-9,9-dimethylacridin-2-
one)))pentaphosphate or dU5P-DDAO
2',3'-Dideoxyadenosine-5'-(ε-7-(9H-(1,3-dichloro-9,9-dimethylacridin-2-
one)))pentaphosphate or ddA5P-DDAO
2',3'-Dideoxyguanosine-5'-(ε-7-(9H-(1,3-dichloro-9,9-dimethylacridin-2-
one)))pentaphosphate or ddG5P-DDAO
2',3'-Dideoxycytidine-5'-(ε-7-(9H-(1,3-dichloro-9,9-dimethylacridin-2-
one)))pentaphosphate or ddC5P-DDAO
2',3'-Dideoxythymidine-5'-(ε-7-(9H-(1,3-dichloro-9,9-dimethylacridin-2-
one)))pentaphosphate or ddT5P-DDAO
2',3'-Dideoxyuridine-5'-(ε-7-(9H-(1,3-dichloro-9,9-dimethylacridin-2-
one)))pentaphosphate or ddU5P-DDAO
3'-Deoxyadenosine-5'-(ε-7-(9H-(1,3-dichloro-9,9-dimethylacridin-2-
one)))pentaphosphate or 3'-dA5P-DDAO
3'-Deoxyguanosine-5'-(ε-7-(9H-(1,3-dichloro-9,9-dimethylacridin-2-
one)))pentaphosphate or 3'-dG5P-DDAO
3'-Deoxycytidine-5'-(ε-7-(9H-(1,3-dichloro-9,9-dimethylacridin-2-
one)))pentaphosphate or 3'-dC5P-DDAO
3'-Deoxythymidine-5'-(ε-7-(9H-(1,3-dichloro-9,9-dimethylacridin-2-
one)))pentaphosphate or 3'-dT5P-DDAO
3'-Deoxyuridine-5'-(ε-7-(9H-(1,3-dichloro-9,9-dimethylacridin-2-
one)))pentaphosphate or 3'-dU5P-DDAO
Adenosine-5'-(ζ-7-(9H-(1,3-dichloro-9,9-dimethylacridin-2-
one)))hexaphosphate or A6P-DDAO
Guanosine-5'-(ζ-7-(9H-(1,3-dichloro-9,9-dimethylacridin-2-
one)))hexaphosphate or G6P-DDAO
Cytidine-5'-(ζ-7-(9H-(1,3-dichloro-9,9-dimethylacridin-2-
one)))hexaphosphate or C6P-DDAO
Thymidine-5'-(ζ-7-(9H-(1,3-dichloro-9,9-dimethylacridin-2-
one)))hexaphosphate or T6P-DDAO
Uridine-5'-(ζ-7-(9H-(1,3-dichloro-9,9-dimethylacridin-2-
one)))hexaphosphate or U6P-DDAO
2'-Deoxyadenosine-5'-(ζ-7-(9H-(1,3-dichloro-9,9-dimethylacridin-2-
one)))hexaphosphate or dA6P-DDAO
2'-Deoxyguanosine-5'-(ζ-7-(9H-(1,3-dichloro-9,9-dimethylacridin-2-
one)))hexaphosphate or dG6P-DDAO
2'-Deoxycytidine-5'-(ζ-7-(9H-(1,3-dichloro-9,9-dimethylacridin-2-
one)))hexaphosphate or dC6P-DDAO
2'-Deoxythymidine-5'-(ζ-7-(9H-(1,3-dichloro-9,9-dimethylacridin-2-
one)))hexaphosphate or dT6P-DDAO
2'-Deoxyuridine-5'-(ζ-7-(9H-(1,3-dichloro-9,9-dimethylacridin-2-
one)))hexaphosphate or dU6P-DDAO
2',3'-Dideoxyadenosine-5'-(ζ-7-(9H-(1,3-dichloro-9,9-dimethylacridin-2-
one)))hexaphosphate or ddA6P-DDAO
2',3'-Dideoxyguanosine-5'-(ζ-7-(9H-(1,3-dichloro-9,9-dimethylacridin-2-
one)))hexaphosphate or ddG6P-DDAO
2',3'-Dideoxycytidine-5'-(ζ-7-(9H-(1,3-dichloro-9,9-dimethylacridin-2-
one)))hexaphosphate or ddC6P-DDAO
2',3'-Dideoxythymidine-5'-(ζ-7-(9H-(1,3-dichloro-9,9-dimethylacridin-2-
one)))hexaphosphate or ddT6P-DDAO
2',3'-Dideoxyuridine-5'-(ζ-7-(9H-(1,3-dichloro-9,9-dimethylacridin-2-
one)))hexaphosphate or ddU6P-DDAO
3'-Deoxyadenosine-5'-(ζ-7-(9H-(1,3-dichloro-9,9-dimethylacridin-2-
one)))hexaphosphate or 3'-dA6P-DDAO
3'-Deoxyguanosine-5'-(ζ-7-(9H-(1,3-dichloro-9,9-dimethylacridin-2-
one)))hexaphosphate or 3'-dG6P-DDAO
3'-Deoxycytidine-5'-(ζ-7-(9H-(1,3-dichloro-9,9-dimethylacridin-2-
one)))hexaphosphate or 3'-dC6P-DDAO
3'-Deoxythymidine-5'-(ζ-7-(9H-(1,3-dichloro-9,9-dimethylacridin-2-
one)))hexaphosphate or 3'-dT6P-DDAO
3'-Deoxyuridine-5'-(ζ-7-(9H-(1,3-dichloro-9,9-dimethylacridin-2-
one)))hexaphosphate or 3'-dU6P-DDAO
Adenosine-5'-(δ-7-umbelliferone)triphosphate or A3P-Umb
Guanosine-5'-(δ-7-umbelliferone)))triphosphate or G3P-Umb
Cytidine-5'-(δ-7-umbelliferone)triphosphate or C3P-Umb
Thymidine-5'-(δ-7-umbelliferone)triphosphate or T3P-Umb
Uridine-5'-(δ-7-umbelliferone)triphosphate or U3P-Umb
2'-Deoxyadenosine-5'-(δ-7-umbelliferone)triphosphate or dA3P-Umb
2'-Deoxyguanosine-5'-(δ-7-umbelliferone)triphosphate or dG3P-Umb
2'-Deoxycytidine-5'-(δ-7-umbelliferone)triphosphate or dC3P-Umb
2'-Deoxythymidine-5'-(δ-7-umbelliferone)triphosphate or dT3P-Umb
2'-Deoxyuridine-5'-(δ-7-umbelliferone)triphosphate or dU3P-Umb

TABLE 3-continued

Some examples of Labeled Nucleoside Polyphosphates where label is directly attached to the polyphosphate chain 2',3'-Dideoxyadenosine-5'-(δ-7-umbelliferone)triphosphate or ddA3P-Umb
2',3'-Dideoxyguanosine-5'-(δ-7-umbelliferone)triphosphate or ddG3P-Umb
2',3'-Dideoxycytidine-5'-(δ-7-umbelliferone)triphosphate or ddC3P-Umb
2',3'-Dideoxythymidine-5'-(δ-7-umbelliferone)triphosphate or ddT3P-Umb
2',3'-Dideoxyuridine-5'-(δ-7-umbelliferone)triphosphate or ddU3P-Umb
3'-Deoxyadenosine-5'-(δ-7-umbelliferone)triphosphate or 3'-dA3P-Umb
3'-Deoxyguanosine-5'-(δ-7-umbelliferone)triphosphate or 3'-dG3P-Umb
3'-Deoxycytidine-5'-(δ-7-umbelliferone)triphosphate or 3'-dC3P-Umb
3'-Deoxythymidine-5'-(δ-7-umbelliferone)triphosphate or 3'-dT3P-Umb
3'-Deoxyuridine-5'-(δ-7-umbelliferone)triphosphate or 3'-dU3P-Umb
Adenosine-5'-(δ-7-umbelliferone)tetraphosphate or A4P-Umb
Guanosine-5'-(δ-7-umbelliferone)))tetraphosphate or G4P-Umb
Cytidine-5'-(δ-7-umbelliferone)tetraphosphate or C4P-Umb
Thymidine-5'-(δ-7-umbelliferone)tetraphosphate or T4P-Umb
Uridine-5'-(δ-7-umbelliferone)tetraphosphate or U4P-Umb
2'-Deoxyadenosine-5'-(δ-7-umbelliferone)tetraphosphate or dA4P-Umb
2'-Deoxyguanosine-5'-(δ-7-umbelliferone)tetraphosphate or dG4P-Umb
2'-Deoxycytidine-5'-(δ-7-umbelliferone)tetraphosphate or dC4P-Umb
2'-Deoxythymidine-5'-(δ-7-umbelliferone)tetraphosphate or dT4P-Umb
2'-Deoxyuridine-5'-(δ-7-umbelliferone)tetraphosphate or dU4P-Umb
2',3'-Dideoxyadenosine-5'-(δ-7-umbelliferone)tetraphosphate or ddA4P-Umb
2',3'-Dideoxyguanosine-5'-(δ-7-umbelliferone)tetraphosphate or ddG4P-Umb
2',3'-Dideoxycytidine-5'-(δ-7-umbelliferone)tetraphosphate or ddC4P-Umb
2',3'-Dideoxythymidine-5'-(δ-7-umbelliferone)tetraphosphate or ddT4P-Umb
2',3'-Dideoxyuridine-5'-(δ-7-umbelliferone)tetraphosphate or ddU4P-Umb
3'-Deoxyadenosine-5'-(δ-7-umbelliferone)tetraphosphate or 3'-dA4P-Umb
3'-Deoxyguanosine-5'-(δ-7-umbelliferone)tetraphosphate or 3'-dG4P-Umb
3'-Deoxycytidine-5'-(δ-7-umbelliferone)tetraphosphate or 3'-dC4P-Umb
3'-Deoxythymidine-5'-(δ-7-umbelliferone)tetraphosphate or 3'-dT4P-Umb
3'-Deoxyuridine-5'-(δ-7-umbelliferone)tetraphosphate or 3'-dU4P-Umb
Adenosine-5'-(ε-7-umbelliferone)pentaphosphate or A5P-Umb
Guanosine-5'-(ε-7-umbelliferone)pentaphosphate or G5P-Umb
Cytidine-5'-(ε-7-umbelliferone)pentaphosphate or C5P-Umb
Thymidine-5'-(ε-7-umbelliferone)pentaphosphate or T5P-Umb
Uridine-5'-(ε-7-umbelliferone)pentaphosphate or U5P-Umb
2'-Deoxyadenosine-5'-(ε-7-umbelliferone)pentaphosphate or dA5P-Umb
2'-Deoxyguanosine-5'-(ε-7-umbelliferone)pentaphosphate or dG5P-Umb
2'-Deoxycytidine-5'-(ε-7-umbelliferone)pentaphosphate or dC5P-Umb
2'-Deoxythymidine-5'-(ε-7-umbelliferone)pentaphosphate or dT5P-Umb
2'-Deoxyuridine-5'-(ε-7-umbelliferone)pentaphosphate or dU5P-Umb
2',3'-Dideoxyadenosine-5'-(ε-7-umbelliferone)pentaphosphate or ddA5P-Umb
2',3'-Dideoxyguanosine-5'-(ε-7-umbelliferone)pentaphosphate or ddG5P-Umb
2',3'-Dideoxycytidine-5'-(ε-7-umbelliferone)pentaphosphate or ddC5P-Umb
2',3'-Dideoxythymidine-5'-(ε-7-umbelliferone)pentaphosphate or ddT5P-Umb
2',3'-Dideoxyuridine-5'-(ε-7-umbelliferone)pentaphosphate or ddU5P-Umb
3'-Deoxyadenosine-5'-(ε-7-umbelliferone)pentaphosphate or 3'-dA5P-Umb
3'-Deoxyguanosine-5'-(ε-7-umbelliferone)pentaphosphate or 3'-dG5P-Umb
3'-Deoxycytidine-5'-(ε-7-umbelliferone)pentaphosphate or 3'-dC5P-Umb
3'-Deoxythymidine-5'-(ε-7-umbelliferone)pentaphosphate or 3'-dT5P-Umb
3'-Deoxyuridine-5'-(ε-7-umbelliferone)pentaphosphate or 3'-dU5P-Umb
Adenosine-5'-(ζ-7-umbelliferone)hexaphosphate or A6P-Umb
Guanosine-5'-(ζ-7-umbelliferone)hexaphosphate or G6P-Umb

TABLE 3-continued

Some examples of Labeled Nucleoside Polyphosphates where label is directly attached to the polyphosphate chain Cytidine-5'-(ζ-7-umbelliferone)hexaphosphate or C6P-Umb
Thymidine-5'-(ζ-7-umbelliferone)hexaphosphate or T6P-Umb
Uridine-5'-(ζ-7-umbelliferone)hexaphosphate or U6P-Umb
2'-Deoxyadenosine-5'-(ζ-7-umbelliferone)hexaphosphate or dA6P-Umb
2'-Deoxyguanosine-5'-(ζ-7-umbelliferone)hexaphosphate or dG6P-Umb
2'-Deoxycytidine-5'-(ζ-7-umbelliferone)hexaphosphate or dC6P-Umb
2'-Deoxythymidine-5'-(ζ-7-umbelliferone)hexaphosphate or dT6P-Umb
2'-Deoxyuridine-5'-(ζ-7-umbelliferone)hexaphosphate or dU6P-Umb
2',3'-Dideoxyadenosine-5'-(ζ-7-umbelliferone)hexaphosphate or ddA6P-Umb
2',3'-Dideoxyguanosine-5'-(ζ-7-umbelliferone)hexaphosphate or ddG6P-Umb
2',3'-Dideoxycytidine-5'-(ζ-7-umbelliferone)hexaphosphate or ddC6P-Umb
2',3'-Dideoxythymidine-5'-(ζ-7-umbelliferone)hexaphosphate or ddT6P-Umb
2',3'-Dideoxyuridine-5'-(ζ-7-umbelliferone)hexaphosphate or ddU6P-Umb
3'-Deoxyadenosine-5'-(ζ-7-umbelliferone)hexaphosphate or 3'-dA6P-Umb
3'-Deoxyguanosine-5'-(ζ-7-umbelliferone)hexaphosphate or 3'-dG6P-Umb
3'-Deoxycytidine-5'-(ζ-7-umbelliferone)hexaphosphate or 3'-dC6P-Umb
3'-Deoxythymidine-5'-(ζ-7-umbelliferone)hexaphosphate or 3'-dT6P-Umb
3'-Deoxyuridine-5'-(ζ-7-umbelliferone)hexaphosphate or 3'-dU6P-Umb
Adenosine-5'-(δ-7-(4-methylumbelliferone)triphosphate or A3P-MeUmb
Guanosine-5'-(δ-7-(4-methylumbelliferone))))triphosphate or G3P-MeUmb
Cytidine-5'-(δ-7-(4-methylumbelliferone))triphosphate or C3P-MeUmb
Thymidine-5'-(δ-7-(4-methylumbelliferone))triphosphate or T3P-MeUmb
Uridine-5'-(δ-7-(4-methylumbelliferone))triphosphate or U3P-MeUmb
2'-Deoxyadenosine-5'-(δ-7-(4-methylumbelliferone))triphosphate or dA3P-MeUmb
2'-Deoxyguanosine-5'-(δ-7-(4-methylumbelliferone))triphosphate or dG3P-MeUmb
2'-Deoxycytidine-5'-(δ-7-(4-methylumbelliferone))triphosphate or dC3P-MeUmb
2'-Deoxythymidine-5'-(δ-7-(4-methylumbelliferone))triphosphate or dT3P-MeUmb
2'-Deoxyuridine-5'-(δ-7-(4-methylumbelliferone))triphosphate or dU3P-MeUmb
2',3'-Dideoxyadenosine-5'-(δ-7-(4-methylumbelliferone))triphosphate or ddA3P-MeUmb
2',3'-Dideoxyguanosine-5'-(δ-7-(4-methylumbelliferone))triphosphate or ddG3P-MeUmb
2',3'-Dideoxycytidine-5'-(δ-7-(4-methylumbelliferone))triphosphate or ddC3P-MeUmb
2',3'-Dideoxythymidine-5'-(δ-7-(4-methylumbelliferone))triphosphate or ddT3P-MeUmb
2',3'-Dideoxyuridine-5'-(δ-7-(4-methylumbelliferone))triphosphate or ddU3P-MeUmb
3'-Deoxyadenosine-5'-(δ-7-(4-methylumbelliferone))triphosphate or 3'-dA3P-MeUmb
3'-Deoxyguanosine-5'-(δ-7-(4-methylumbelliferone))triphosphate or 3'-dG3P-MeUmb
3'-Deoxycytidine-5'-(δ-7-(4-methylumbelliferone))triphosphate or 3'-dC3P-MeUmb
3'-Deoxythymidine-5'-(δ-7-(4-methylumbelliferone))triphosphate or 3'-dT3P-MeUmb
3'-Deoxyuridine-5'-(δ-7-(4-methylumbelliferone))triphosphate or 3'-dU3P-MeUmb
Adenosine-5'-(δ-7-(4-methylumbelliferone))tetraphosphate or A4P-MeUmb
Guanosine-5'-(δ-7-(4-methylumbelliferone))))tetraphosphate or G4P-MeUmb
Cytidine-5'-(δ-7-(4-methylumbelliferone))tetraphosphate or C4P-MeUmb
Thymidine-5'-(δ-7-(4-methylumbelliferone))tetraphosphate or T4P-MeUmb TABLE 3-continued Some examples of Labeled Nucleoside Polyphosphates where label is directly attached to the polyphosphate chain Uridine-5'-(δ-7-(4-methylumbelliferone))tetraphosphate or U4P-MeUmb
2'-Deoxyadenosine-5'-(δ-7-(4-methylumbelliferone))tetraphosphate or dA4P-MeUmb
2'-Deoxyguanosine-5'-(δ-7-(4-methylumbelliferone))tetraphosphate or dG4P-MeUmb
2'-Deoxycytidine-5'-(δ-7-(4-methylumbelliferone))tetraphosphate or dC4P-MeUmb
2'-Deoxythymidine-5'-(δ-7-(4-methylumbelliferone))tetraphosphate or dT4P-MeUmb
2'-Deoxyuridine-5'-(δ-7-(4-methylumbelliferone))tetraphosphate or dU4P-MeUmb
2',3'-Dideoxyadenosine-5'-(δ-7-(4-methylumbelliferone))tetraphosphate or ddA4P-MeUmb
2',3'-Dideoxyguanosine-5'-(δ-7-(4-methylumbelliferone))tetraphosphate or ddG4P-MeUmb
2',3'-Dideoxycytidine-5'-(δ-7-(4-methylumbelliferone))tetraphosphate or ddC4P-MeUmb
2',3'-Dideoxythymidine-5'-(δ-7-(4-methylumbelliferone))tetraphosphate or ddT4P-MeUmb
2',3'-Dideoxyuridine-5'-(δ-7-(4-methylumbelliferone))tetraphosphate or ddU4P-MeUmb
3'-Deoxyadenosine-5'-(δ-7-(4-methylumbelliferone))tetraphosphate or 3'-dA4P-MeUmb
3'-Deoxyguanosine-5'-(δ-7-(4-methylumbelliferone))tetraphosphate or 3'-dG4P-MeUmb
3'-Deoxycytidine-5'-(δ-7-(4-methylumbelliferone))tetraphosphate or 3'-dC4P-MeUmb
3'-Deoxythymidine-5'-(δ-7-(4-methylumbelliferone))tetraphosphate or 3'-dT4P-MeUmb
3'-Deoxyuridine-5'-(δ-7-(4-methylumbelliferone))tetraphosphate or 3'-dU4P-MeUmb
Adenosine-5'-(ε-7-(4-methylumbelliferone))pentaphosphate or A5P-MeUmb
Guanosine-5'-(ε-7-(4-methylumbelliferone))pentaphosphate or G5P-MeUmb
Cytidine-5'-(ε-7-(4-methylumbelliferone))pentaphosphate or C5P-MeUmb
Thymidine-5'-(ε-7-(4-methylumbelliferone))pentaphosphate or T5P-MeUmb
Uridine-5'-(ε-7-(4-methylumbelliferone))pentaphosphate or U5P-MeUmb
2'-Deoxyadenosine-5'-(ε-7-(4-methylumbelliferone))pentaphosphate or dA5P-MeUmb
2'-Deoxyguanosine-5'-(ε-7-(4-methylumbelliferone))pentaphosphate or dG5P-MeUmb
2'-Deoxycytidine-5'-(ε-7-(4-methylumbelliferone))pentaphosphate or dC5P-MeUmb
2'-Deoxythymidine-5'-(ε-7-(4-methylumbelliferone))pentaphosphate or dT5P-MeUmb
2'-Deoxyuridine-5'-(ε-7-(4-methylumbelliferone))pentaphosphate or dU5P-MeUmb
2',3'-Dideoxyadenosine-5'-(ε-7-(4-methylumbelliferone))pentaphosphate or ddA5P-MeUmb
2',3'-Dideoxyguanosine-5'-(ε-7-(4-methylumbelliferone))pentaphosphate or ddG5P-MeUmb
2',3'-Dideoxycytidine-5'-(ε-7-(4-methylumbelliferone))pentaphosphate or ddC5P-MeUmb
2',3'-Dideoxythymidine-5'-(ε-7-(4-methylumbelliferone))pentaphosphate or ddT5P-MeUmb
2',3'-Dideoxyuridine-5'-(ε-7-(4-methylumbelliferone))pentaphosphate or ddU5P-MeUmb
3'-Deoxyadenosine-5'-(ε-7-(4-methylumbelliferone))pentaphosphate or 3'-dA5P-MeUmb
3'-Deoxyguanosine-5'-(ε-7-(4-methylumbelliferone))pentaphosphate or 3'-dG5P-MeUmb
3'-Deoxycytidine-5'-(ε-7-(4-methylumbelliferone))pentaphosphate or 3'-dC5P-MeUmb
3'-Deoxythymidine-5'-(ε-7-(4-methylumbelliferone))pentaphosphate or 3'-dT5P-MeUmb
3'-Deoxyuridine-5'-(ε-7-(4-methylumbelliferone))pentaphosphate or 3'-dU5P-MeUmb
Adenosine-5'-(ζ-7-(4-methylumbelliferone))hexaphosphate or A6P-MeUmb
Guanosine-5'-(ζ-7-(4-methylumbelliferone))hexaphosphate or G6P-MeUmb TABLE 3-continued Some examples of Labeled Nucleoside Polyphosphates where label is directly attached to the polyphosphate chain Cytidine-5'-(ζ-7-(4-methylumbelliferone))hexaphosphate or C6P-MeUmb
Thymidine-5'-(ζ-7-(4-methylumbelliferone))hexaphosphate or T6P-MeUmb
Uridine-5'-(ζ-7-(4-methylumbelliferone))hexaphosphate or U6P-MeUmb
2'-Deoxyadenosine-5'-(ζ-7-(4-methylumbelliferone))hexaphosphate or dA6P-MeUmb
2'-Deoxyguanosine-5'-(ζ-7-(4-methylumbelliferone))hexaphosphate or dG6P-MeUmb
2'-Deoxycytidine-5'-(ζ-7-(4-methylumbelliferone))hexaphosphate or dC6P-MeUmb
2'-Deoxythymidine-5'-(ζ-7-(4-methylumbelliferone))hexaphosphate or dT6P-MeUmb
2'-Deoxyuridine-5'-(ζ-7-(4-methylumbelliferone))hexaphosphate or dU6P-MeUmb
2',3'-Dideoxyadenosine-5'-(ζ-7-(4-methylumbelliferone))hexaphosphate or ddA6P-MeUmb
2',3'-Dideoxyguanosine-5'-(ζ-7-(4-methylumbelliferone))hexaphosphate or ddG6P-MeUmb
2',3'-Dideoxycytidine-5'-(ζ-7-(4-methylumbelliferone))hexaphosphate or ddC6P-MeUmb
2',3'-Dideoxythymidine-5'-(ζ-7-(4-methylumbelliferone))hexaphosphate or ddT6P-MeUmb
2',3'-Dideoxyuridine-5'-(ζ-7-(4-methylumbelliferone))hexaphosphate or ddU6P-MeUmb
3'-Deoxyadenosine-5'-(ζ-7-(4-methylumbelliferone))hexaphosphate or 3'-dA6P-MeUmb
3'-Deoxyguanosine-5'-(ζ-7-(4-methylumbelliferone))hexaphosphate or 3'-dG6P-MeUmb
3'-Deoxycytidine-5'-(ζ-7-(4-methylumbelliferone))hexaphosphate or 3'-dC6P-MeUmb
3'-Deoxythymidine-5'-(ζ-7-(4-methylumbelliferone))hexaphosphate or 3'-dT6P-MeUmb
3'-Deoxyuridine-5'-(ζ-7-(4-methylumbelliferone))hexaphosphate or 3'-dU6P-MeUmb
Adenosine-5'-(δ-7-resorufin)triphosphate or A3P-RR
Guanosine-5'-(δ-7-resorufin))triphosphate or G3P-RR
Cytidine-5'-(δ-7-resorufin)triphosphate or C3P-RR
Thymidine-5'-(δ-7-resorufin)triphosphate or T3P-RR
Uridine-5'-(δ-7-resorufin)triphosphate or U3P-RR
2'-Deoxyadenosine-5'-(δ-7-resorufin) triphosphate or dA3P-RR
2'-Deoxyguanosine-5'-(δ-7-resorufin) triphosphate or dG3P-RR
2'-Deoxycytidine-5'-(δ-7-resorufin) triphosphate or dC3P-RR
2'-Deoxythymidine-5'-(δ-7-resorufin) triphosphate or dT3P-RR
2'-Deoxyuridine-5'-(δ-7-resorufin) triphosphate or dU3P-RR
2',3'-Dideoxyadenosine-5'-(δ-7-resorufin)triphosphate or ddA3P-RR
2',3'-Dideoxyguanosine-5'-(δ-7-resorufin)triphosphate or ddG3P-RR
2',3'-Dideoxycytidine-5'-(δ-7-resorufin)triphosphate or ddC3P-RR
2',3'-Dideoxythymidine-5'-(δ-7-resorufin)triphosphate or ddT3P-RR
2',3'-Dideoxyuridine-5'-(δ-7-resorufin)triphosphate or ddU3P-RR
3'-Deoxyadenosine-5'-(δ-7-resorufin) triphosphate or 3'-dA3P-RR
3'-Deoxyguanosine-5'-(δ-7-resorufin) triphosphate or 3'-dG3P-RR
3'-Deoxycytidine-5'-(δ-7-resorufin) triphosphate or 3'-dC3P-RR
3'-Deoxythymidine-5'-(δ-7-resorufin) triphosphate or 3'-dT3P-RR
3'-Deoxyuridine-5'-(δ-7-resorufin) triphosphate or 3'-dU3P-RR
Adenosine-5'-(δ-7-resorufin)tetraphosphate or A4P-RR
Guanosine-5'-(δ-7-resorufin)))tetraphosphate or G4P-RR
Cytidine-5'-(δ-7-resorufin)tetraphosphate or C4P-RR
Thymidine-5'-(δ-7-resorufin)tetraphosphate or T4P-RR
Uridine-5'-(δ-7-resorufin)tetraphosphate or U4P-RR
2'-Deoxyadenosine-5'-(δ-7-resorufin) tetraphosphate or dA4P-RR
2'-Deoxyguanosine-5'-(δ-7-resorufin) tetraphosphate or dG4P-RR
2'-Deoxycytidine-5'-(δ-7-resorufin) tetraphosphate or dC4P-RR
2'-Deoxythymidine-5'-(δ-7-resorufin) tetraphosphate or dT4P-RR
2'-Deoxyuridine-5'-(δ-7-resorufin) tetraphosphate or dU4P-RR
2',3'-Dideoxyadenosine-5'-(δ-7-resorufin)tetraphosphate or ddA4P-RR
2',3'-Dideoxyguanosine-5'-(δ-7-resorufin)tetraphosphate or ddG4P-RR
2',3'-Dideoxycytidine-5'-(δ-7-resorufin)tetraphosphate or ddC4P-RR
2',3'-Dideoxythymidine-5'-(δ-7-resorufin)tetraphosphate or ddT4P-RR
2',3'-Dideoxyuridine-5'-(δ-7-resorufin)tetraphosphate or ddU4P-RR
3'-Deoxyadenosine-5'-(δ-7-resorufin) tetraphosphate or 3'-dA4P-RR
3'-Deoxyguanosine-5'-(δ-7-resorufin) tetraphosphate or 3'-dG4P-RR

TABLE 3-continued

Some examples of Labeled Nucleoside Polyphosphates where label is directly attached to the polyphosphate chain 3'-Deoxycytidine-5'-(δ-7-resorufin) tetraphosphate or 3'-dC4P-RR
3'-Deoxythymidine-5'-(δ-7-resorufin) tetraphosphate or 3'-dT4P-RR
3'-Deoxyuridine-5'-(δ-7-resorufin) tetraphosphate or 3'-dU4P-RR
Adenosine-5'-(ε-7-resorufin)pentaphosphate or A5P-RR
Guanosine-5'-(ε-7-resorufin)pentaphosphate or G5P-RR
Cytidine-5'-(ε-7-resorufin)pentaphosphate or C5P-RR
Thymidine-5'-(ε-7-resorufin)pentaphosphate or T5P-RR
Uridine-5'-(ε-7-resorufin)pentaphosphate or U5P-RR
2'-Deoxyadenosine-5'-(ε-7-resorufin)pentaphosphate or dA5P-RR
2'-Deoxyguanosine-5'-(ε-7-resorufin)pentaphosphate or dG5P-RR
2'-Deoxycytidine-5'-(ε-7-resorufin) pentaphosphate or dC5P-RR
2'-Deoxythymidine-5'-(ε-7-resorufin) pentaphosphate or dT5P-RR
2'-Deoxyuridine-5'-(ε-7-resorufin) pentaphosphate or dU5P-RR
2',3'-Dideoxyadenosine-5'-(ε-7-resorufin)pentaphosphate or ddA5P-RR
2',3'-Dideoxyguanosine-5'-(ε-7-resorufin)pentaphosphate or ddG5P-RR
2',3'-Dideoxycytidine-5'-(ε-7-resorufin)pentaphosphate or ddC5P-RR
2',3'-Dideoxythymidine-5'-(ε-7-resorufin)pentaphosphate or ddT5P-RR
2',3'-Dideoxyuridine-5'-(ε-7-resorufin)pentaphosphate or ddU5P-RR
3'-Deoxyadenosine-5'-(ε-7-resorufin) pentaphosphate or 3'-dA5P-RR
3'-Deoxyguanosine-5'-(ε-7-resorufin) pentaphosphate or 3'-dG5P-RR
3'-Deoxycytidine-5'-(ε-7-resorufin) pentaphosphate or 3'-dC5P-RR
3'-Deoxythymidine-5'-(ε-7-resorufin) pentaphosphate or 3'-dT5P-RR
3'-Deoxyuridine-5'-(ε-7-resorufin) pentaphosphate or 3'-dU5P-RR
Adenosine-5'-(ζ-7-resorufin)hexaphosphate or A6P-RR
Guanosine-5'-(ζ-7-resorufin)hexaphosphate or G6P-RR
Cytidine-5'-(ζ-7-resorufin)hexaphosphate or C6P-RR
Thymidine-5'-(ζ-7-resorufin)hexaphosphate or T6P-RR
Uridine-5'-(ζ-7-resorufin)hexaphosphate or U6P-RR
2'-Deoxyadenosine-5'-(ζ-7-resorufin) hexaphosphate or dA6P-RR
2'-Deoxyguanosine-5'-(ζ-7-resorufin) hexaphosphate or dG6P-RR
2'-Deoxycytidine-5'-(ζ-7-resorufin)hexaphosphate or dC6P-RR
2'-Deoxythymidine-5'-(ζ-7-resorufin)hexaphosphate or dT6P-RR
2'-Deoxyuridine-5'-(ζ-7-resorufin)hexaphosphate or dU6P-RR
2',3'-Dideoxyadenosine-5'-(ζ-7-resorufin)hexaphosphate or ddA6P-RR
2',3'-Dideoxyguanosine-5'-(ζ-7-resorufin)hexaphosphate or ddG6P-RR
2',3'-Dideoxycytidine-5'-(ζ-7-resorufin)hexaphosphate or ddC6P-RR
2',3'-Dideoxythymidine-5'-(ζ-7-resorufin)hexaphosphate or ddT6P-RR
2',3'-Dideoxyuridine-5'-(ζ-7-resorufin)hexaphosphate or ddU6P-RR
3'-Deoxyadenosine-5'-(ζ-7-resorufin) hexaphosphate or 3'-dA6P-RR
3'-Deoxyguanosine-5'-(ζ-7-resorufin)hexaphosphate or 3'-dG6P-RR
3'-Deoxycytidine-5'-(ζ-7-resorufin)hexaphosphate or 3'-dC6P-RR
3'-Deoxythymidine-5'-(ζ-7-resorufin)hexaphosphate or 3'-dT6P-RR
3'-Deoxyuridine-5'-(ζ-7-resorufin)hexaphosphate or 3'-dU6P-RR
Adenosine-5'-(δ-3'-(6'-ethylfluorescein)triphosphate or A3P-FlEt
Guanosine-5'-(δ-3'-(6'-ethylfluorescein))))triphosphate or G3P-FlEt
Cytidine-5'-(δ-3'-(6'-ethylfluorescein))triphosphate or C3P-FlEt
Thymidine-5'-(δ-3'-(6'-ethylfluorescein))triphosphate or T3P-FlEt
Uridine-5'-(δ-3'-(6'-ethylfluorescein))triphosphate or U3P-FlEt
2'-Deoxyadenosine-5'-(δ-3'-(6'-ethylfluorescein))triphosphate or dA3P-FlEt
2'-Deoxyguanosine-5'-(δ-3'-(6'-ethylfluorescein))triphosphate or dG3P-FlEt
2'-Deoxycytidine-5'-(δ-3'-(6'-ethylfluorescein))triphosphate or dC3P-FlEt
2'-Deoxythymidine-5'-(δ-3'-(6'-ethylfluorescein))triphosphate or dT3P-FlEt
2'-Deoxyuridine-5'-(δ-3'-(6'-ethylfluorescein))triphosphate or dU3P-FlEt
2',3'-Dideoxyadenosine-5'-(δ-3'-(6'-ethylfluorescein))triphosphate or ddA3P-FlEt
2',3'-Dideoxyguanosine-5'-(δ-3'-(6'-ethylfluorescein))triphosphate or ddG3P-FlEt
2',3'-Dideoxycytidine-5'-(δ-3'-(6'-ethylfluorescein))triphosphate or ddC3P-FlEt
2',3'-Dideoxythymidine-5'-(δ-3'-(6'-ethylfluorescein))triphosphate or ddT3P-FlEt
2',3'-Dideoxyuridine-5'-(δ-3'-(6'-ethylfluorescein))triphosphate or ddU3P-FlEt
3'-Deoxyadenosine-5'-(δ-3'-(6'-ethylfluorescein))triphosphate or 3'-dA3P-FlEt
3'-Deoxyguanosine-5'-(δ-3'-(6'-ethylfluorescein))triphosphate or 3'-dG3P-FlEt
3'-Deoxycytidine-5'-(δ-3'-(6'-ethylfluorescein))triphosphate or 3'-dC3P-FlEt
3'-Deoxythymidine-5'-(δ-3'-(6'-ethylfluorescein))triphosphate or 3'-dT3P-FlEt

TABLE 3-continued

Some examples of Labeled Nucleoside Polyphosphates where label is directly attached to the polyphosphate chain 3'-Deoxyuridine-5'-(δ-3'-(6'-ethylfluorescein))triphosphate or 3'-dU3P-FlEt
Adenosine-5'-(δ-3'-(6'-ethylfluorescein))tetraphosphate or A4P-FlEt
Guanosine-5'-(δ-3'-(6'-ethylfluorescein))))tetraphosphate or G4P-FlEt
Cytidine-5'-(δ-3'-(6'-ethylfluorescein))tetraphosphate or C4P-FlEt
Thymidine-5'-(δ-3'-(6'-ethylfluorescein))tetraphosphate or T4P-FlEt
Uridine-5'-(δ-3'-(6'-ethylfluorescein))tetraphosphate or U4P-FlEt
2'-Deoxyadenosine-5'-(δ-3'-(6'-ethylfluorescein))tetraphosphate or dA4P-FlEt
2'-Deoxyguanosine-5'-(δ-3'-(6'-ethylfluorescein))tetraphosphate or dG4P-FlEt
2'-Deoxycytidine-5'-(δ-3'-(6'-ethylfluorescein))tetraphosphate or dC4P-FlEt
2'-Deoxythymidine-5'-(δ-3'-(6'-ethylfluorescein))tetraphosphate or dT4P-FlEt
2'-Deoxyuridine-5'-(δ-3'-(6'-ethylfluorescein))tetraphosphate or dU4P-FlEt
2',3'-Dideoxyadenosine-5'-(δ-3'-(6'-ethylfluorescein))tetraphosphate or ddA4P-FlEt
2',3'-Dideoxyguanosine-5'-(δ-3'-(6'-ethylfluorescein))tetraphosphate or ddG4P-FlEt
2',3'-Dideoxycytidine-5'-(δ-3'-(6'-ethylfluorescein))tetraphosphate or ddC4P-FlEt
2',3'-Dideoxythymidine-5'-(δ-3'-(6'-ethylfluorescein))tetraphosphate or ddT4P-FlEt
2',3'-Dideoxyuridine-5'-(δ-3'-(6'-ethylfluorescein))tetraphosphate or ddU4P-FlEt
3'-Deoxyadenosine-5'-(δ-3'-(6'-ethylfluorescein))tetraphosphate or 3'-dA4P-FlEt
3'-Deoxyguanosine-5'-(δ-3'-(6'-ethylfluorescein))tetraphosphate or 3'-dG4P-FlEt
3'-Deoxycytidine-5'-(δ-3'-(6'-ethylfluorescein))tetraphosphate or 3'-dC4P-FlEt
3'-Deoxythymidine-5'-(δ-3'-(6'-ethylfluorescein))tetraphosphate or 3'-dT4P-FlEt
3'-Deoxyuridine-5'-(δ-3'-(6'-ethylfluorescein))tetraphosphate or 3'-dU4P-FlEt
Adenosine-5'-(ε-3'-(6'-ethylfluorescein))pentaphosphate or A5P-FlEt
Guanosine-5'-(ε-3'-(6'-ethylfluorescein))pentaphosphate or G5P-FlEt
Cytidine-5'-(ε-3'-(6'-ethylfluorescein))pentaphosphate or C5P-FlEt
Thymidine-5'-(ε-3'-(6'-ethylfluorescein))pentaphosphate or T5P-FlEt
Uridine-5'-(ε-3'-(6'-ethylfluorescein))pentaphosphate or U5P-FlEt
2'-Deoxyadenosine-5'-(ε-3'-(6'-ethylfluorescein))pentaphosphate or dA5P-FlEt
2'-Deoxyguanosine-5'-(ε-3'-(6'-ethylfluorescein))pentaphosphate or dG5P-FlEt
2'-Deoxycytidine-5'-(ε-3'-(6'-ethylfluorescein))pentaphosphate or dC5P-FlEt
2'-Deoxythymidine-5'-(ε-3'-(6'-ethylfluorescein))pentaphosphate or dT5P-FlEt
2'-Deoxyuridine-5'-(ε-3'-(6'-ethylfluorescein))pentaphosphate or dU5P-FlEt
2',3'-Dideoxyadenosine-5'-(ε-3'-(6'-ethylfluorescein))pentaphosphate or ddA5P-FlEt
2',3'-Dideoxyguanosine-5'-(ε-3'-(6'-ethylfluorescein))pentaphosphate or ddG5P-FlEt
2',3'-Dideoxycytidine-5'-(ε-3'-(6'-ethylfluorescein))pentaphosphate or ddC5P-FlEt
2',3'-Dideoxythymidine-5'-(ε-3'-(6'-ethylfluorescein))pentaphosphate or ddT5P-FlEt
2',3'-Dideoxyuridine-5'-(ε-3'-(6'-ethylfluorescein))pentaphosphate or ddU5P-FlEt
3'-Deoxyadenosine-5'-(ε-3'-(6'-ethylfluorescein))pentaphosphate or 3'-dA5P-FlEt
3'-Deoxyguanosine-5'-(ε-3'-(6'-ethylfluorescein))pentaphosphate or 3'-dG5P-FlEt
3'-Deoxycytidine-5'-(ε-3'-(6'-ethylfluorescein))pentaphosphate or 3'-dC5P-FlEt
3'-Deoxythymidine-5'-(ε-3'-(6'-ethylfluorescein))pentaphosphate or 3'-dT5P-FlEt
3'-Deoxyuridine-5'-(ε-3'-(6'-ethylfluorescein))pentaphosphate or 3'-dU5P-FlEt
Adenosine-5'-(ζ-3'-(6'-ethylfluorescein))hexaphosphate or A6P-FlEt
Guanosine-5'-(ζ-3'-(6'-ethylfluorescein))hexaphosphate or G6P-FlEt
Cytidine-5'-(ζ-3'-(6'-ethylfluorescein))hexaphosphate or C6P-FlEt
Thymidine-5'-(ζ-3'-(6'-ethylfluorescein))hexaphosphate or T6P-FlEt

TABLE 3-continued

Some examples of Labeled Nucleoside Polyphosphates where label is directly attached to the polyphosphate chain Uridine-5'-(ζ-3'-(6'-ethylfluorescein))hexaphosphate or U6P-FlEt
2'-Deoxyadenosine-5'-(ζ-3'-(6'-ethylfluorescein)) hexaphosphate or dA6P-FlEt
2'-Deoxyguanosine-5'-(ζ-3'-(6'-ethylfluorescein))hexaphosphate or dG6P-FlEt
2'-Deoxycytidine-5'-(ζ-3'-(6'-ethylfluorescein))hexaphosphate or dC6P-FlEt
2'-Deoxythymidine-5'-(ζ-3'-(6'-ethylfluorescein))hexaphosphate or dT6P-FlEt
2'-Deoxyuridine-5'-(ζ-3'-(6'-ethylfluorescein))hexaphosphate or dU6P-FlEt
2',3'-Dideoxyadenosine-5'-(ζ-3'-(6'-ethylfluorescein))hexaphosphate or ddA6P-FlEt
2',3'-Dideoxyguanosine-5'-(ζ-3'-(6'-ethylfluorescein))hexaphosphate or ddG6P-FlEt
2',3'-Dideoxycytidine-5'-(ζ-3'-(6'-ethylfluorescein))hexaphosphate or ddC6P-FlEt
2',3'-Dideoxythymidine-5'-(ζ-3'-(6'-ethylfluorescein))hexaphosphate or ddT6P-FlEt
2',3'-Dideoxyuridine-5'-(ζ-3'-(6'-ethylfluorescein))hexaphosphate or ddU6P-FlEt
3'-Deoxyadenosine-5'-(ζ-3'-(6'-ethylfluorescein))hexaphosphate or 3'-dA6P-FlEt
3'-Deoxyguanosine-5'-(ζ-3'-(6'-ethylfluorescein))hexaphosphate or 3'-dG6P-FlEt
3'-Deoxycytidine-5'-(ζ-3'-(6'-ethylfluorescein))hexaphosphate or 3'-dC6P-FlEt
3'-Deoxythymidine-5'-(ζ-3'-(6'-ethylfluorescein))hexaphosphate or 3'-dT6P-FlEt
3'-Deoxyuridine-5'-(ζ-3'-(6'-ethylfluorescein))hexaphosphate or 3'-dU6P-FlEt

TABLE 4

Some examples of terminal -phosphate labeled nucleotides with labels that are detectable without removal of phosphate FAM-amidoheptyl-gamma-amido-deoxyguanosine-triphosphate
ROX-amidoheptyl-gamma-amido-deoxyguanosine-triphosphate
REG-amidoheptyl-gamma-amido-deoxyguanosine-triphosphate
R110-amidoheptyl-gamma-amido-deoxyguanosine-triphosphate
TAMRA-amidoheptyl-gamma-amido-deoxyguanosine-triphosphate
ROX-amidoheptyl-gamma-amido-thymidine-triphosphate
REG-amidoheptyl-gamma-amido-thymidine-triphosphate
R110-amidoheptyl-gamma-amido-thymidine-triphosphate
TAMRA-amidoheptyl-gamma-amido-thymidine-triphosphate
ROX-amidoheptyl-gamma-amido-deoxycytidine-triphosphate
REG-amidoheptyl-gamma-amido-deoxycytidine-triphosphate
R110-amidoheptyl-gamma-amido-deoxycytidine-triphosphate
TAMRA-amidoheptyl-gamma-amido-deoxycytidine-triphosphate
ROX-amidoheptyl-gamma-amido-deoxyadenosine-triphosphate
REG-amidoheptyl-gamma-amido-deoxyadenosine-triphosphate
R110-amidoheptyl-gamma-amido-deoxyadenosine-triphosphate
TAMRA-amidoheptyl-gamma-amido-deoxyadenosine-triphosphate
ROX-amidopropyl-gamma-amido-deoxyadenosine-triphosphate
REG-amidopropyl-gamma-amido-deoxyadenosine-triphosphate
R110-amidopropyl-gamma-amido-deoxyadenosine-triphosphate
TAMRA-amidopropyl-gamma-amido-thymidine-triphosphate
TAMRA-amidododecyl-gamma-amido-thymidine-triphosphate
TAMRA-amidocyclohexyl-gamma-amido-thymidine-triphosphate
TAMRA-amidoxylene-gamma-amido-thymidine-triphosphate
FAM-amidoheptyl-gamma-amido-deoxyguanosine-tetraphosphate
ROX-amidoheptyl-gamma-amido-deoxyguanosine-tetraphosphate
REG-amidoheptyl-gamma-amido-deoxyguanosine-tetraphosphate
R110-amidoheptyl-gamma-amido-deoxyguanosine-tetraphosphate
TAMRA-amidoheptyl-gamma-amido-deoxyguanosine-tetraphosphateCy3-amidoheptyl-gamma-amido-deoxyguanosine-5'-tetraphosphate
Cy5-amidoheptyl-gamma-amido-deoxyguanosine-5'-tetraphosphate
Alexa-amidoheptyl-gamma-amido-deoxyguanosine-5'-tetraphosphate
FAM-amido-triethyleneglycol-deoxyadedosine-5'-triphosphate
FAM-amido-triethyleneglycol-deoxyguanosine-5'-triphosphate
REG-amido-triethyleneglycol-deoxyguanosine-5'-triphosphate
TAMRA-amido-triethyleneglycol-deoxyguanosine-5'-triphosphate

TABLE 4-continued

Some examples of terminal -phosphate labeled nucleotides with labels that are detectable without removal of phosphate ROX-amido-triethyleneglycol-deoxyguanosine-5'-triphosphate
Cy3-amido-triethyleneglycol-deoxyguanosine-5'-triphosphate
Cy5-amido-triethyleneglycol-deoxyguanosine-5'-triphosphate
Cy5-amido-triethyleneglycol-deoxyguanosine-5'-tetraphosphate
TAMRA-amido-triethyleneglycol-deoxyguanosine-5'-tetraphosphate
ROX-amido-tetraethyleneglycol-deoxyguanosine-5'-tetraphosphate
Cy3-amido-tetraethyleneglycol-deoxyguanosine-5'-tetraphosphate
TAMRA-amido-tetraethyleneglycol-deoxyguanosine-5'-tetraphosphate
TAMRA-amido-tetraethyleneglycol-deoxyguanosine-5'-pentaphosphate
TAMRA-(Lys)n-amidoheptyl-amido-deoxyguanosine-5'-tetraphosphate
TAMRA-(Lys)n-amidoheptyl-amido-thymidine-5'-tetraphosphate When the phosphorylated label in Formula I is a fluorogenic moiety, it is desirably selected from one of the following (all shown as the phosphomonester): 2-(5'-chloro-2'-phosphoryloxyphenyl)-6-chloro-4-(3H)-quinazolinone, sold under the trade name ELF 97 (Molecular Probes, Inc.), fluorescein diphosphate (tetraammonium salt), fluorescein 3'(6')-O-alkyl-6'(3')-phosphate, 9H-(1,3-dichloro-9,9-dimethylacridin-2-one-7-yl)phosphate (diammonium salt), 4-methylumbelliferyl phosphate (free acid), resorufin phosphate, 4-trifluoromethylumbelliferyl phosphate, umbelliferyl phosphate, 3-cyanoubelliferyl phosphate, 9,9-dimethylacridin-2-one-7-yl phosphate, 6,8-difluoro-4-methylumbelliferyl phosphate and derivatives thereof. Structures of these dyes are shown below:

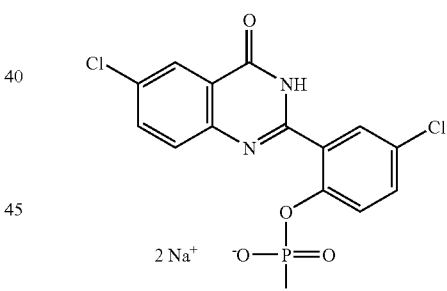

2-(5'-chloro-2'-phosphoryloxyphenyl)-6-chloro-4-(3H)-quinazolinone

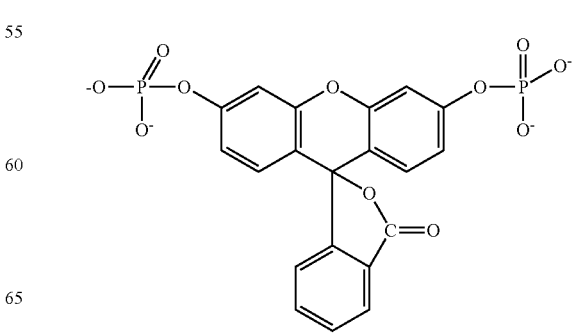

-continued
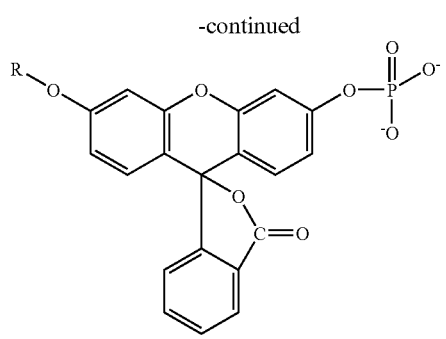
fluorescein diphosphate fluorescein 3'(6')-O-alkyl-6'(3')-phosphate
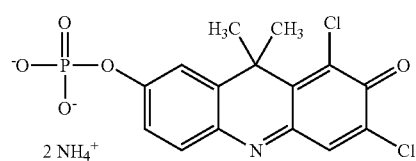
9H-(1,3-dichloro-9,9-dimethylacridin-2-one-7-yl)phosphate (diammonium salt)
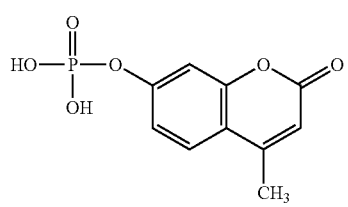
4-methylumbelliferyl phosphate
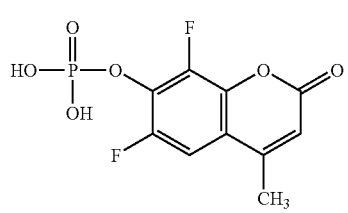
6,8-difluoro-4-methylumbelliferyl phosphate
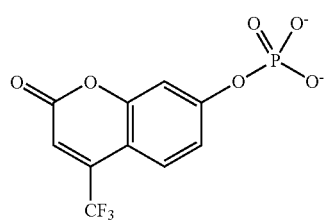
4-Trifluoromethylumbelliferyl phosphate
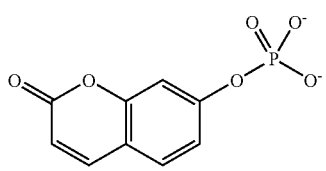
Umbelliferyl phosphate
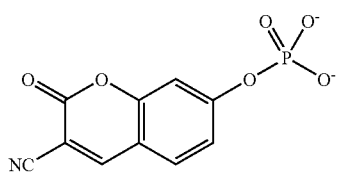
3-Cyanoumbelliferyl phosphate
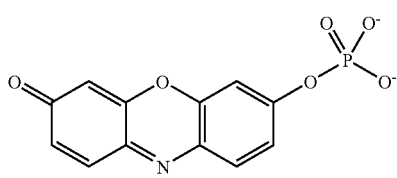
Resorufin phosphate
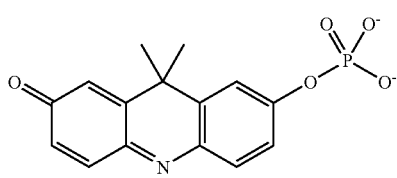

9,9-dimethylacridin-2-one-7-yl phosphate

When the phosphorylated label moiety in Formula I above is a chromogenic moiety, it may be selected from the following: 5-bromo-4-chloro-3-indolyl phosphate, 3-indoxyl phosphate, p-nitrophenyl phosphate and derivatives thereof. The structures of these chromogenic dyes are shown as the phosphomonoesters below:

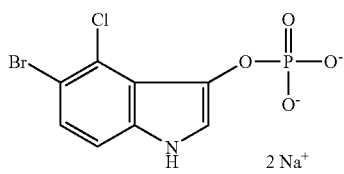

5-bromo-4-chloro-3-indolyl phosphate (disodium salt)

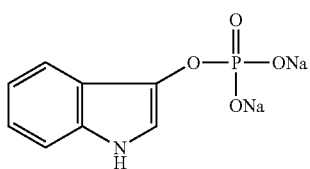

3-indolyl phosphate (disodium salt)

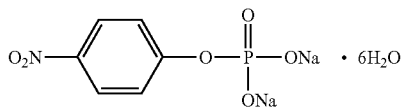

p-nitrophenyl phosphate

The moiety at the terminal-phosphate position may further be a chemiluminescent compound wherein it is desired that it is a phosphatase-activated 1,2-dioxetane compound. The 1,2-dioxetane compound may include, but is not limited to, disodium 2-chloro-5-(4-methoxyspiro[1,2-dioxetane-3,2'-(5-chloro-)tricyclo[3,3,1-1$^{3,7}$]-decan]-1-yl)-1-phenyl phosphate, sold under the trade name CDP-Star (Tropix, Inc., Bedford, Mass.), chloroadamant-2'-ylidenemethoxyphenoxy phosphorylated dioxetane, sold under the trade name CSPD (Tropix), and 3-(2'-spiroadamantane)-4-methoxy-4-(3''-phosphoryloxy)phenyl-1,2-dioxetane, sold under the trade name AMPPD (Tropix). The structures of these commercially available dioxetane compounds are disclosed in U.S. Pat. Nos. 5,582,980, 5,112,960 and 4,978,614, respectively, and are incorporated herein by reference.

A few examples of terminal phosphate labeled nucleotides with dyes that are detectable without removal of phosphate and are well incorporated into DNA by polymerases in the presence of a manganese salt and that are within the structural formula are shown below.

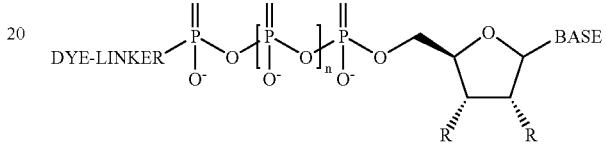

wherein some examples of possible linkers are:

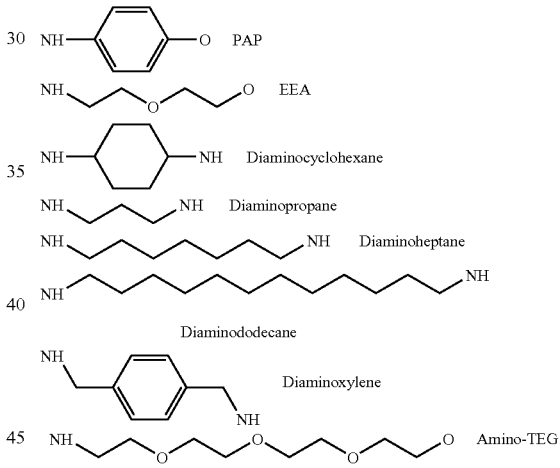

Peptide With 1-10 Aminoacids Such as Glycine, Glycylglycylglysine, Pentalysine, Decalysine, Glycylalanine, Glycylleucine, Betainyllysine, etc.

as well as combination of above moieties to form a linker. An example of latter is shown below.

R=H or OH
Base=A, G, C, T, U, or modified derivatives thereof
n=1-4
Dye=Fluorescein, rhodamine, Alexa Cyanine, merrocyanine, Bodipy Coumarin, phenoxazines, acridines, acridones
Dye may also be an energy-transfer cassette made of a donor dye and an acceptor dye as shown in the second example below.

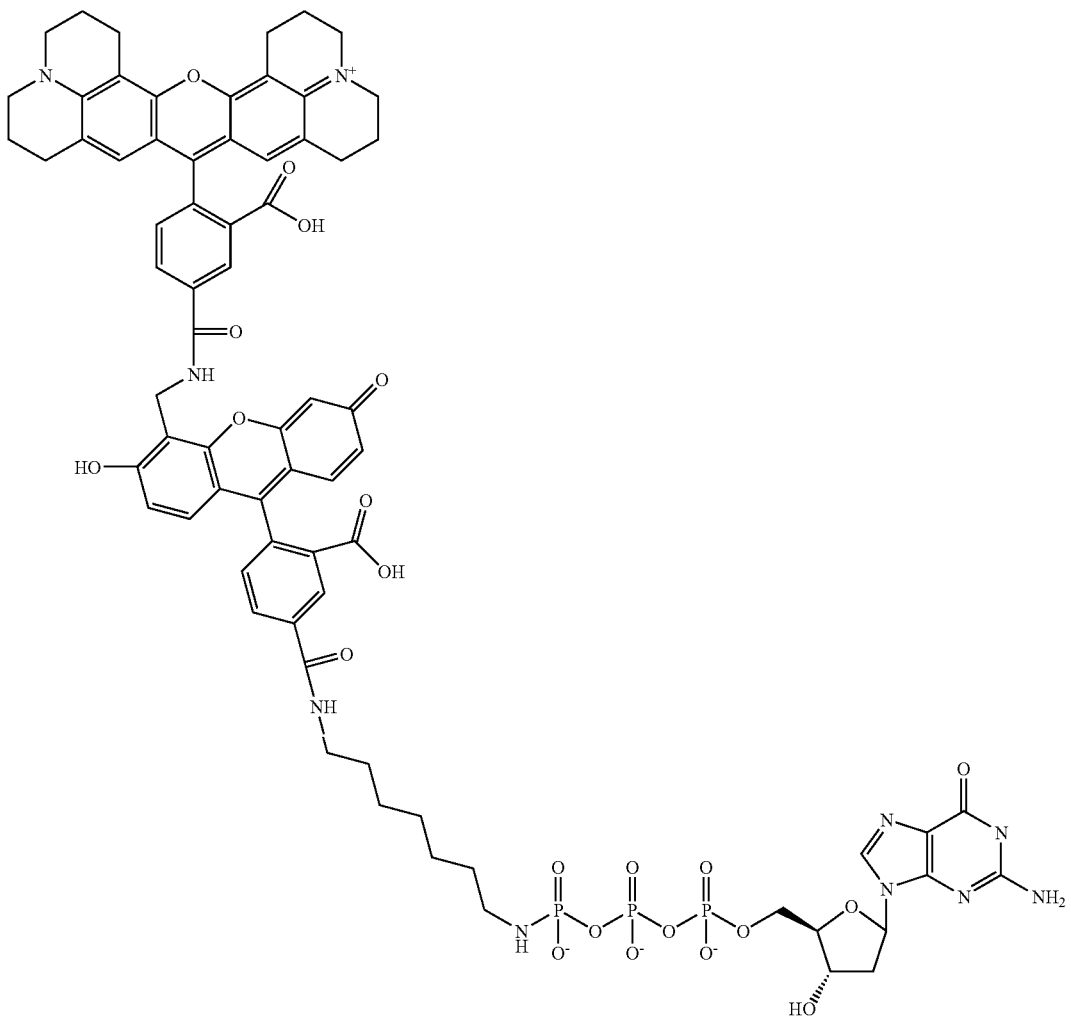

ROX-FAM-Aminoheptyl Gamma dGTP Phosphoramidate [A Terminal-phosphate Labeled Nucleoside Polyphosphate With an Energy Transfer Donor-acceptor Dye Pair as the Label]

The present invention further includes a nucleic acid detection kit wherein the kit includes:

a) at least one or more terminal-phosphate-labeled nucleotide according to Formula I:

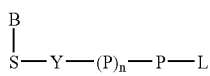

wherein P=phosphate (PO$_3$) and derivatives thereof, n is 2 or greater; Y is an oxygen or sulfur atom; B is a nitrogen-containing heterocyclic base; S is an acyclic moiety, carbocyclic moiety or sugar moiety; P-L is a phosphorylated label which becomes independently detectable when the phosphate is removed, wherein L is an enzyme-activatable label containing a hydroxyl group, a sulfhydryl group or an amino group suitable for forming a phosphate ester, a thioester, or a phosphoramidate linkage at the terminal phosphate of a natural or modified nucleotide;

b) at least one of DNA polymerase, RNA polymerase, or reverse transcriptase;
c) phosphatase; and
d) reaction buffer containing a manganese salt.

The present invention further includes a nucleic acid detection kit wherein the kit includes:

a) at least one or more terminal-phosphate-labeled nucleotide according to Formula I:

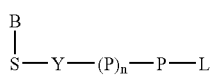

wherein P=phosphate (PO$_3$) and derivatives thereof, n is 2 or greater; Y is an oxygen or sulfur atom; B is a nitrogen-containing heterocyclic base; S is an acyclic moiety, carbocyclic moiety or sugar moiety; P-L is a phosphorylated label with a linker between L and P, wherein L is a label containing a hydroxyl group, a sulfhydryl group, a haloalkyl group or an amino group suitable for forming a phosphate ester, a thioester, an alkylphosphonate or a phosphoramidate linkage at the terminal phosphate of a natural or modified nucleotide;
b) at least one of DNA polymerase, RNA polymerase, or reverse transcriptase; and
c) a reaction buffer containing a manganese salt.

Further provided is a nucleic acid detection kit comprising:
a) at least one manganese complex of a terminal-phosphate labeled nucleoside polyphosphate of formula II;

Label-NPP-(Mn)$_x$ wherein Label is a detectable moiety linked to NPP with or without a linker, NPP is a nucleoside polyphosphate with four or more phosphates, and x is 1 or more; and
b) a nucleic acid polymerase.

Also provided is a nucleic acid detection kit comprising:
a) at least one manganese complex of a terminal-phosphate labeled nucleoside polyphosphate of formula II;

Label-NPP-(Mn)$_x$ wherein Label is a detectable moiety linked to NPP with or without a linker, NPP is a nucleoside polyphosphate with four or more phosphates, and x is 1 or more;
b) a nucleic acid polymerase; and
c) a metal-ion binding buffer.

The sugar moiety in the terminal-phosphate-labeled nucleotide or its manganese complex included in the kit may include, but is not limited to ribosyl, 2'-deoxyribosyl, 3'-deoxyribosyl, 2',3'-dideoxyribosyl, 2',3'-didehydrodideoxyribosyl, 2'- or 3'-alkoxyribosyl, 2'- or 3'-aminoribosyl, 2'- or 3'-fluororibosyl, 2'- or 3'-mercaptoribosyl, 2'- or 3'-alkylthioribosyl, acyclic, carbocyclic and other modified sugars.

The base may be, but is not limited to uracil, thymine, cytosine, 5-methylcytosine, guanine, 7-deazaguanine, hypoxanthine, 7-deazahypoxanthine, adenine, 7-deazaadenine and 2,6-diaminopurine and analogs thereof.

Furthermore, as described above, the enzyme-activatable label may be a 1,2-dioxetane chemiluminescent compound, fluorescent dye, chromogenic dye, a mass tag, an electrochemical tag or a combination thereof. Suitable compounds for conjugation at the terminal-phosphate position of the nucleotide are the same as those described above. Additionally, the label may be a detectable label that doesn't require activation by phosphatase.

Compounds of the present invention may be synthesized by methods described in the schemes below.

Synthesis of terminal-phosphate-labeled nucleoside triphosphates:

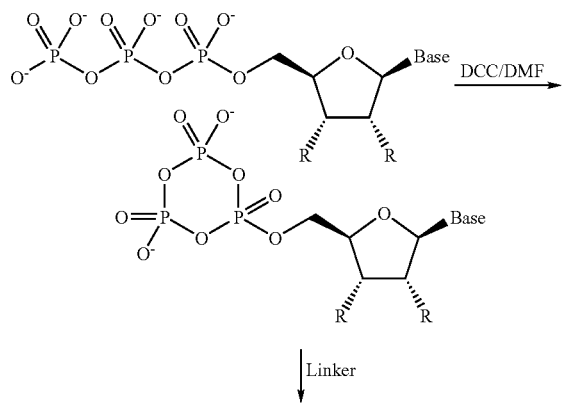

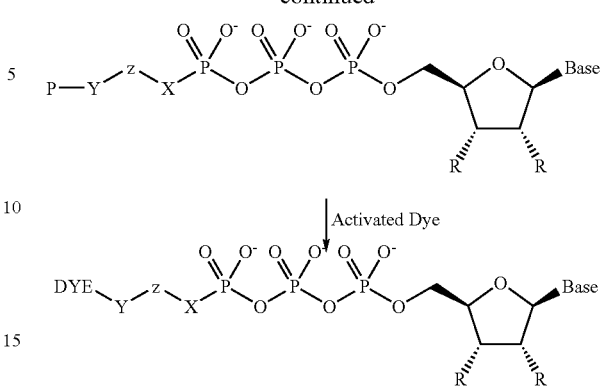

wherein X is NH, O, S or CH$_2$,
Y is NH, O, S, ONH, CH$_2$, CO or another functional group capable of forming a covalent bond with the dye moiety and P is H or a leaving group such as halide or sulfonate.

Synthesis of terminal-phosphate-labeled nucleoside-5'-tetraphosphates:

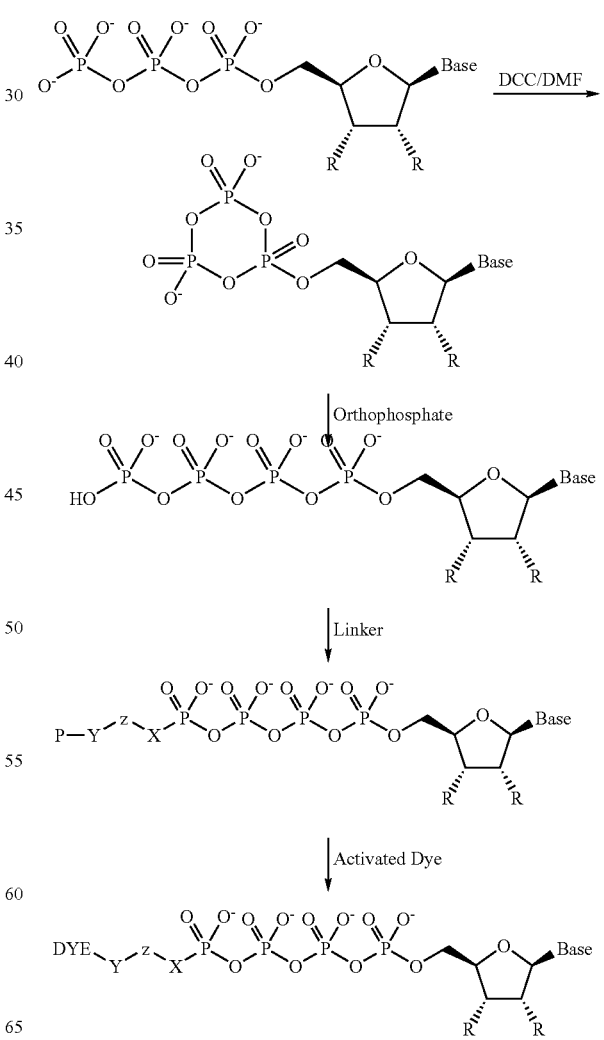

wherein X is NH, O, S, or CH$_2$,
Y is NH, O, S, ONH, CO, CH$_2$ or another functional group capable of forming a covalent bond with the dye moiety and P is H or a leaving group such as halide or sulfonate.

Synthesis of terminal-phosphate-labeled nucleoside-5'-pentaphosphates:

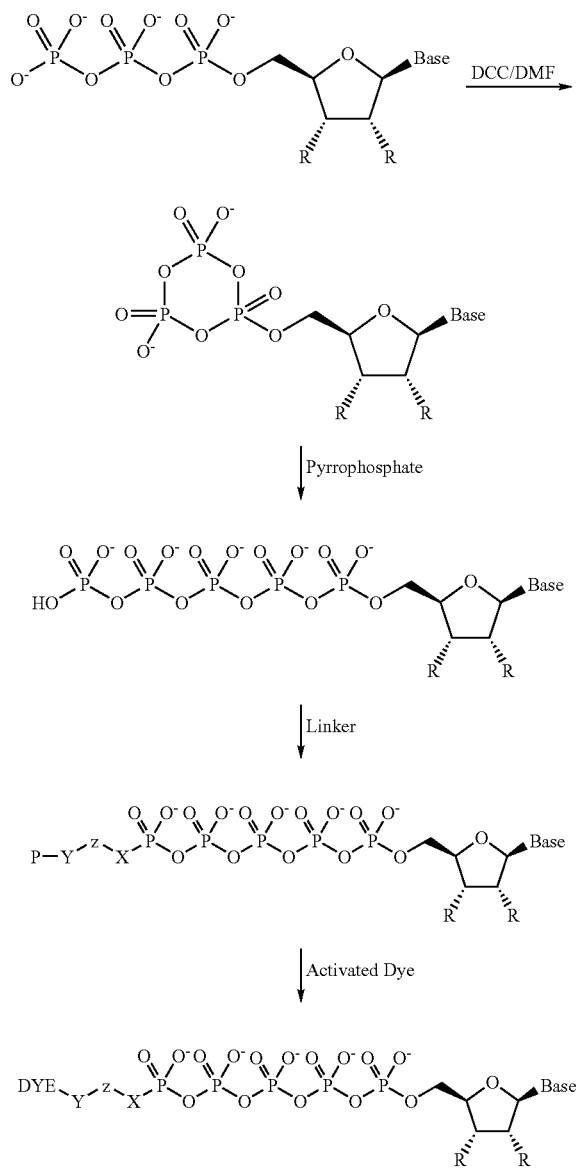

wherein X is NH, O, S, or CH$_2$,
Y is NH, O, S, ONH, CH$_2$, CO or another functional group capable of forming a covalent bond with the dye moiety and P is H or a leaving group such as halide or sulfonate.

The invention is further described by reference to the examples below.

EXAMPLES

The following examples illustrate certain preferred embodiments of the instant invention but are not intended to be illustrative of all embodiments. These examples should not be construed as limiting the appended claims and/or the scope of this invention.

Example 1

Preparation of γ-(4-trifluoromethylcoumarinyl)ddGTP (γCF$_3$Coumarin-ddGTP)

ddGTP (200 ul of 46.4 mM solution, purity >96%) was coevaporated with anhydrous dimethylformamide (DMF, 2×0.5 ml). To this dicyclohexylcarbodiimide (DCC, 9.6 mg, 5 eq.) was added and mixture was again coevaporated with anhyd. DMF (0.5 ml). Residue was taken in anhyd. DMF (0.5 ml) and mixture was allowed to stir overnight. There was still ca 20% uncyclized triphosphate (could be from hydrolysis of cyclic trimetaphosphate on the column). To the mixture another 2 eq. of DCC was added and after stirring for 2 h, 7-hydroxy-4-trifluoromethyl coumarin (4-trifluoromethylumbelliferone, 42.7 mg, 20 eq.) and triethylamine (26 ul, 20 eq.) were added and mixture was stirred at RT. After 2 days, HPLC (0-30% acetonitrile in 0.1M triethylammonium acetate (TEAA) in 15 minutes, 30-50% acetonitrile in 5 min and 50-100% acetonitrile in 10 minutes, C18 3.9×150 mm column, flow rate 1 ml/minute) showed a new product at 9.7 min and starting cyclic triphosphate (ratio of 77 to 5 at 254 nm). Mixture was allowed to stir for another day. P-31 NMR showed gamma labeled nucleoside-triphosphate as the main component of reaction mixture. Reaction mixture was concentrated on rotary evaporator. Residue was extracted with water (5×1 ml). HPLC showed a purity of 82% at 254 nm and 81% at 335 nm. Combined aq solution was conc. on rotary evaporator and redissolved in water (1 ml). It was purified on 1 inch×300 cm C18 column using 0-30% acetonitrile in 0.1M triethylammonium bicarbonate (TEAB, pH 8.3) in 30 min and 30-50% acetonitrile in 10 min, 15 ml/min flow rate. Product peak was collected in 3 fractions. Fraction 1 was repurified using the same preparative HPLC method as above except the pH of the TEAB buffer was reduced to 6.7 by bubbling CO$_2$. Product peak was concentrated and coevaporated with MeOH (2 times) and water (1 time). Sample was dissolved in 1 ml water. HPLC showed a purity of >99% at 254 and 335 nm. UV showed a conc. of 2.2 mM assuming an extinction coeff. of 11,000 at 322 nm (reported for beta galactoside derivative of 7-hydroxy-4-trifluoromethylcoumarin, Molecular Probes Catalog). MS: M$^-$=702.18 (calc 702.31), UV $\lambda_A$=253, 276 & 322 nm. The trifluorocoumarin dye attached to the gamma phosphate of ddGTP is fluorescent with an excitation maximum of 322 nm and an emission maximum of about 415 nm. Upon hydrolysis of the phosphate ester to release the free coumarin dye, the spectrum changes with excitation maximum of about 385 nm and emission maximum of about 502 nm. This change is readily detected by simple fluorescence measurements or color change. Synthesis of gamma nucleotides has been generally described by Arzumanov, A. et al. in J Biol Chem (1996) October 4; 271 (40): 24389-94.

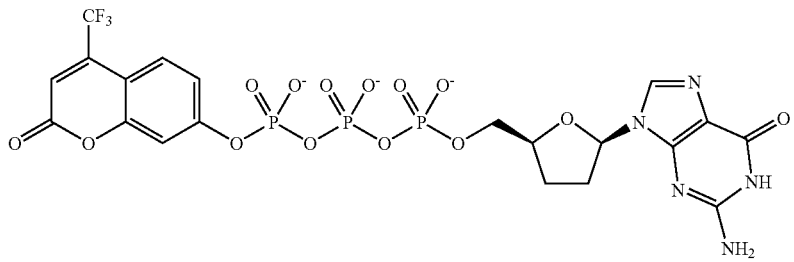

γ-(4-trifluoromethylcoumarinyl)dideoxyguanosine-5'-triphosphate (γCF₃Coumarin-ddGTP)

Example 2

Preparation of γ-(3-Cyanocoumarinyl)ddATP (γCNCoumarin-ddATP)

ddATP (100 μl of 89 mM solution, >96%) was coevaporated with anhydrous DMF (2×1 ml). To this DCC (9.2 mg, 5 eq.) was added and mixture was again coevaporated with anhydrous DMF (1 ml). Residue was taken in anhydrous DMF (0.5 ml) and reaction was stirred at rt. After overnight 7-hydroxy-3-cyanocoumarin (33.3 mg, 20 eq.) and TEA (25 ul, 20 eq.), were added and mixture was stirred at RT. After 1 day, a major product (55% at 254 nm) was observed 8.1 min with another minor product at 10 min (~10%). No significant change occurred after another day. Reaction mixture was concentrated on rotary evaporator and residue was extracted with 3×2 ml water and filtered. Aq solution was concentrated and purified on C-18 using 0-30% acetonitrile in 0.1M TEAB (pH 6.7) in 30 min and 30-50% acetonitrile in 10 min, flow rate 15 ml/min. Main peak was collected in 3 fractions. HPLC of the main peak (fr. 2) showed a purity of 95.6% at 254 nm and 98.1% at 335 nm. It was concentrated on rotary evaporator (at RT), coevaporated with MeOH (2×) and water (1×). Residue was dissolved in 0.5 ml water. A 5 ul sample was diluted to 1 ml for UV analysis. A346 nm=0.784. Assuming an extinction coeff. of 20,000 (reported for 7-ethoxy-3-cyanocoumarin, Molecular Probes Catalog), concentration=7.84 mM. Yield=3.92 mmol, 44%. Sample was repurified on C-18 column using same method as above. Sample peak was collected in 3 fractions. Fractions 2 & 3, with >98% purity at 254 nm and >99.5% purity at 340 nm, were combined. After concentration, residue was coevaporated with MeOH (2×) and water (1×). Sample was dissolved in water (1 ml) to give a 2.77 mM solution. MS: M⁻=642.98 au (calc 643.00 au), UV $\lambda_A$=263 & 346 nm The cyanocoumarin dye attached to the gamma phosphate of ddATP is fluorescent with an excitation maximum of 346 nm and an emission maximum of about 411 nm. Upon hydrolysis of the phosphate ester to release the free coumarin dye, the spectrum changes with excitation maximum of about 408 nm and emission maximum of about 450 nm. This change is readily detected by simple fluorescence measurements or color change. Synthesis of gamma nucleotides has been generally described by Arzumanov, A, et al in J. Biol. Chem. (1996) October 4;271 (40):24389-94.

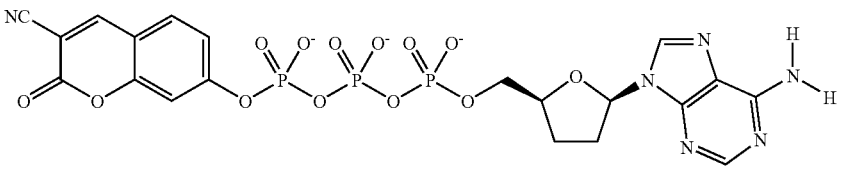

γ-(3-cyanocoumarinyl)dideoxyadenosine-5'-triphosphate (γCNCoumarin-ddATP)

Example 3

Preparation of δ-9H(1,3-dichloro-9,9-dimethylacridin-2-one-7-yl)-dideoxythymidine-5'-tetraphosphate (ddT4P-DDAO)

ddTTP (100 μl of 80 mM solution) was coevaporated with anhydrous dimethylformamide (DMF, 2×1 ml). To this dicyclohexylcarbodimide (8.3 mg. 5 eq.) was added and the mixture was again coevaporated with anhydrous DMF (1 ml). Residue was taken in anhydrous DMF (1 ml) and reaction was stirred at room temperature overnight. HPLC showed mostly cyclized triphosphate (~82%). Reaction mixture was concentrated and residue was washed with anhydrous diethyl ether 3×. It was redissolved in anhydrous DMF and concentrated to dryness on rotavap. Residue was taken with DDAO-monophosphate, ammonium salt (5 mg, 1.5 eq.) in 200 μl anhydrous DMF and stirred at 40° C. over the weekend. HPLC showed formation of a new product with desired UV characteristics at 11.96 min. (HPLC Method: 0.30% acetonitrile in 0.1M triethylammonium acetate (pH 7) in 15 min, and 30-50% acetonitrile in 5 min, Novapak C-18 3.9×150 mm column, 1 ml/min). LCMS (ES-) also showed a major mass peak 834 for M−1 peak. Reaction mixture was concentrated and purified on Deltapak C18, 19×300 mm column using 0.1M TEAB (pH 6.7) and acetonitrile. Fraction with product was repurified by HPLC using the same method as described above. Fraction with pure product was concentrated, coevaporated with MeOH (2×) and water (1×). Residue was dissolved in water (1.2 ml) to give a 1.23 mM solution. HPCL purity as 254 nm>97.5%, at 455 nm>96%; UV $\lambda_A$=267 nm and 455 nm; MS: M−1=834.04 (calc 8.33.95). δ-9H(1,3- dichloro-9,9-dimethylacridin-2-one-7-yl)-dideoxycytidine-5'-tetraphosphate (ddC4P-DDAO), δ-9H(1,3-dichloro-9,9-dimethylacridin-2-one-dideoxyadenosine-5'-tetraphosphate (ddA4P-DDAO) and δ-9H(1,3-dichloro-9,9-dimethylacridin-2-one-yl)-dideoxyguanosine-5'-tetraphosphate (ddG4P-DDAO) were synthesized and purified in a similar fashion.

Analysis of these purified compounds provided the following data: ddC4P-DDAO: UV $\lambda_A$=268 nm and 454 nm; MS: M−1=819.32 (calc 818.96); ddA4P-DDAO: UV $\lambda_A$=263 nm and 457 nm; MS: M−1=843.30 (calc 842.97); ddG4P-DDAO: UV $\lambda_A$=257 nm and 457 nm; MS: M−1=859.40 (calc 858.97).

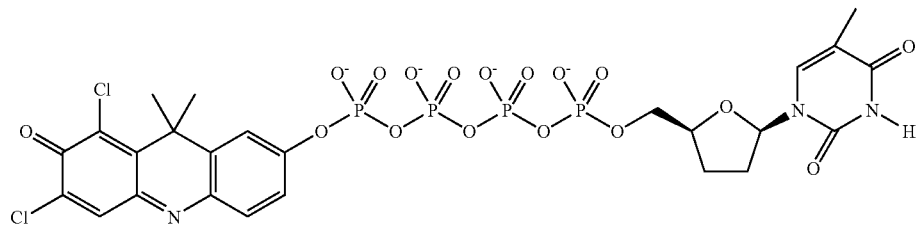

ddT4P-DDAO

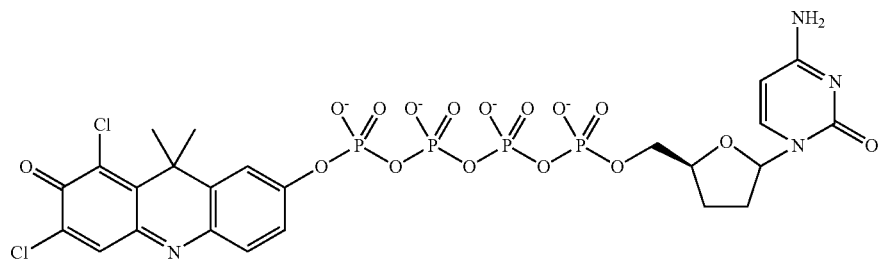

ddC4P-DDAO

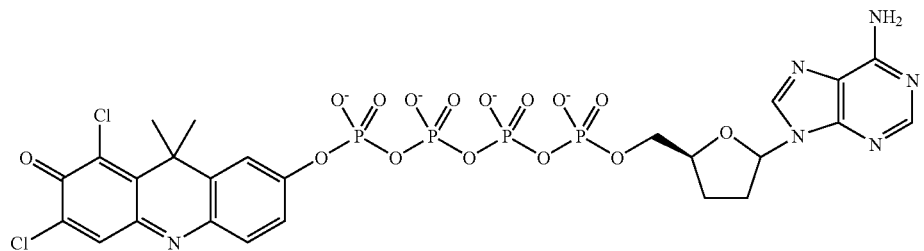

ddA4P-DDAO

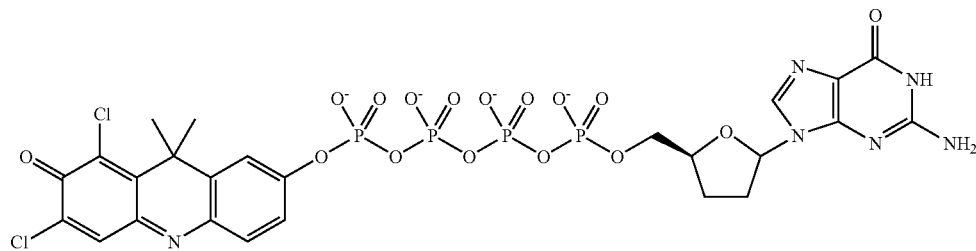

ddG4P-DDAO

Example 4

Preparation of ε-9H (1,3-dichloro-9,9-dimethylacridin-2-one-7-yl)-dideoxythymidine-5'-pentaphosphate DDAO-ddT-pentaphosphate (ddT5P-DDAO)

A. Preparation of DDAO Pyrophosphate

DDAO-phosphate diammonium salt (11.8 mmol) was coevaporated with anhydrous DMF (3×0.25 ml) and was dissolved in DMF (0.5 ml). To this carbonyldiimidazole (CDI, 9.6 mg, 5 eq) was added and the mixture was stirred at room temperature overnight. Excess CDI was destroyed by addition of MeOH (5 ul) and stirring for 30 minutes. To the mixture tributylammoniumdihydrogen phosphate (10 eq., 236 ml of 0.5 M solution in DMF) was added and the mixture was stirred at room temperature for 4 days. Reaction mixture was concentrated on rotavap. Residue was purified on HiPrep 16.10 Q XL column using 0-100% B using 0.1 M TEAB/acetonitrle (3:1) as buffer A and 1 M TEAB/acetonitrile (3:1) as buffer B. Main peak (HPLC purity 98%) was collected, concentrated and coevaporated with methanol (2×). Residue was dissolved in 1 ml water to give 5.9 mM solution. UV/VIS $\lambda_{max}$=456 nm.

B. Preparation of ddT5P-DDAO ddTTP (100 ul of 47.5 mM solution in water) was coevaporated with anhydrous DMF (2×1 ml). To this DCC (5 eq., 4.9 mg) was added and mixture was coevaporated with DMF (1×1 ml). Residue was taken in anhydrous DMF (0.5 ml) and stirred at room temperature for 3 hours. To this 1.03 eq of DDAO pyrophosphate, separately coevaporated with anhydrous DMF (2×1 ml) was added as a DMF solution. Mixture was concentrated to dryness and then taken in 200 ul anhydrous DMF. Mixture was heated at 38° C. for 2 days. Reaction mixture was concentrated, diluted with water, filtered and purified on HiTrap 5 ml ion exchange column using 0-100% A-B using a two step gradient. Solvent A=0.1 M TEAB/acetonitrile (3:1) and solvent B=1M TEAB/acetonitrile (3:1). Fraction 12×13 which contained majority of product were combined, concentrated and coevaporated with methanol (2×). Residue was repurified on Xterra RP C-18 30-100 mm column using 0.30% acetonitrile in 0.1M TEAB in 5 column and 30-50% acetonitrile in 2 column volumes, flow rate 10 ml/min. Fraction containing pure product was concentrated and coevaporated with methanol (2×) and water (1×). HPLC purity at 455 nm>99%. UV/VIS=268 nm and 455 nm. MS: M−1=914.03 (calc 913.93).

The DDAO dye attached to the terminal phosphate of these polyphosphates is fluorescent with an excitation maximum of 455 nm and an emission maximum of about 608 nm. Upon hydrolysis of the phosphate ester to release the free dye, the spectrum changes with excitation maximum of about 645 nm and emission maximum of about 659 nm. The change is readily detected by simple fluorescence measurements or color change.

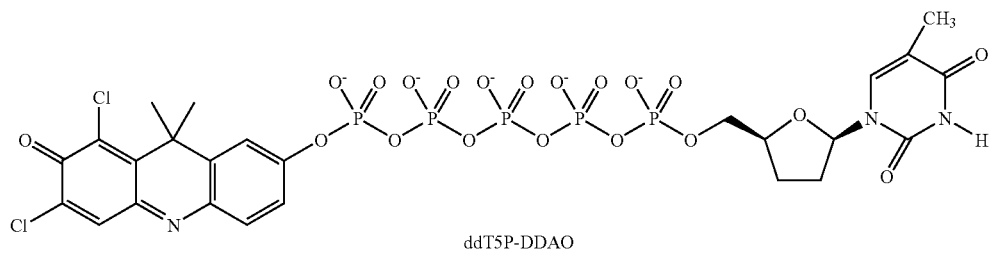

ddT5P-DDAO

Example 5

A) Synthesis of dCTP-diaminoheptyl-REG (dCTP-NH(CH$_2$)$_7$-NH-REG or dCTP-DAH-REG

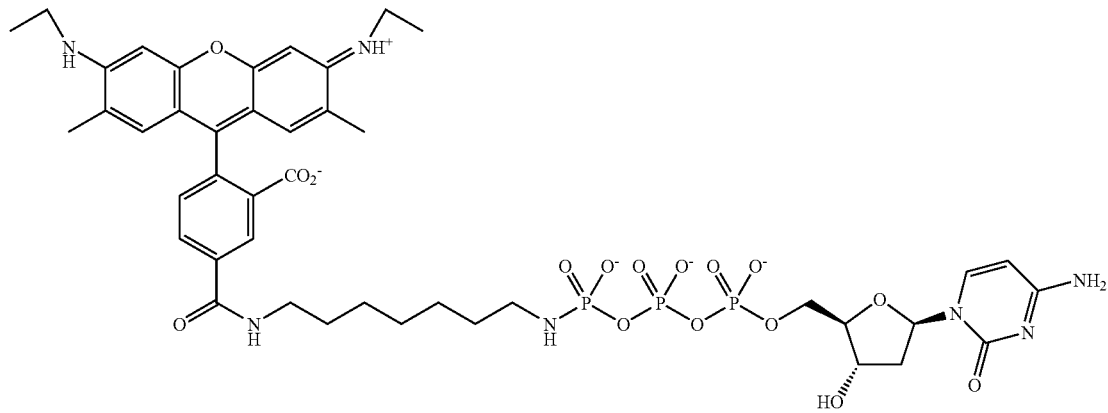

a: 10 μmoles dCTP-triethylammonium salt was combined with 40 μmoles tributylamine and evaporated to dryness. The residue was coevaporated to dryness 2 times with anhydrous DMF. This was redissolved in 1 ml DMF and 50 μmoles of DCC was added, followed by evaporation to dryness. The mixture was dissolved in 1 ml anhydrous DMF and stirred overnight at ambient temperature.

b: 500 μmoles Diaminoheptane was dissolved in 5 ml anhydrous DMF and was evaporated to dryness. This was followed by 2 coevaporations with dry DMF. The residue was dissolved in 2 ml dry DMF. This solution was combined with the DCC-dCTP reaction (after 16 hr DCC-dCTP reaction time). After 4 hr HPLC showed 86% conversion to Diaminoheptyl dCTP.

The reaction was diluted to 25 ml with water and adjusted to pH 12 with NaOH. The mixture was extracted twice with diethylether. The aqueous layer was evaporated to remove ether. The compound was purified on a 19×300 Delta pak column using 0.1M TEAB/Acetonitrile gradient. The fractions showing pure dCTP-NH(CH$_2$)$_7$NH$_2$ were combined and concentrated to dryness. The residue was coevaporated 2 times with ethanol. The compound was redissolved in water (2 ml). Yield by UV/Vis spectrophotometry was 6.4 μmoles.

Analytical HPLC on Xterra RP C18 4.6×150 mm column 0.1M TEAB/MeCN gradient (0-15% MeCN) in 15 min: retention time 4.55 min. $\lambda_{max}$ 270 nm.

c: 1 μmole dCTP-diaminoheptane (from above) was diluted to 400 ul in 0.1M NaHCO$_3$ pH 9.3. To this was added 2 μmoles 5-REG NHS ester in 200 μl DMF. The reaction proceeded at ambient temperature for 2 hr. The reaction was diluted to 10 ml with water and applied to a HR10/10 Mono Q column. The column was eluted with a gradient from 0.1M TEAB/25% Acetonitrile to 1M TEAB/25% acetonitrile. The fractions containing dCTP-DAH-REG were combined and concentrated to dryness, followed by coevaporation 2 times with ethanol. The product was dissolved in water giving a yield of 190 nmoles.

B) Synthesis of dA4P-diaminoheptyl-TAMRA (dA4P-NH(CH$_2$)$_7$-NH-TAMRA

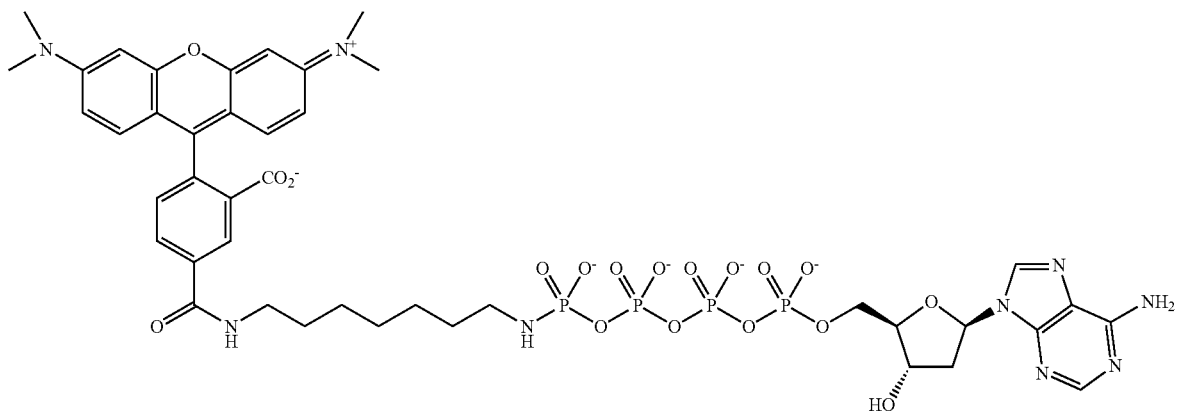

a: Synthesis of dA4P: 200 μmoles TEA dATP was combined with 1 mMole Tributylamine and concentrated to dryness. The residue was coevaporated once with anhydrous pyridine and once with dry DMF. The dATP was redissolved in 5 ml dry DMF and 1 mMole Cabonyldiimidazole was added. The reaction was stirred for 4 hr. After 4 hr, 8 μl methanol was added and stirred for 30 min. Next, 1 mmole TBA H$_2$PO$_4$ was added and the reaction was stirred at ambient temperature overnight.

The reaction was diluted to 25 ml with water and was purified on a Q Sepharose XL 16/10 column using 0.1M TEAB to 1M TEAB gradient pH 6.8. The fractions containing product were applied to a Xterra RP C18 19×100 column and eluted with a 0.1 mTEAB/Acetonitrile gradient. The fractions containing pure product were concentrated to dryness and coevaporated 2 times with methanol. The dA4P was assayed by HPLC (Xterra RP C18 4.6×150 0.1M TEAA/MeCN 0-40% in 12 min) 98% purity. Retention time 4.95 min. Yield 110 μmoles.

b: Synthesis of dA4P-Diaminoheptyl: The following reagents were combined:

50 μmoles dA4P in 2 ml water, 2.5 ml 0.2M 1-methylimidazole-HCl pH6, 96 mg EDAC, and 162 mg Diaminoheptane. The pH was adjusted to 6 with HCl and the reaction was allowed to proceed 5 hr. The reaction was diluted to 50 ml with water and applied to a Q Sepharose XL 16/10 column and was eluted with a 0-100% 0.1M TEAB/1M TEAB gradient. The fractions containing pure product were combined concentrated to dryness and coevaporated 2 times with methanol. HPLC: Xterra RP C18 0-80% 0.1M TEAA/Acetonitrile in 12 min Purity 85%. Retention time 4.4 min. Yield 7 μmoles c: Synthesis of dA4P-diaminoheptyl-TAMRA: 2.5 μmoles dA4P-diaminoheptyl was dissolved in 500 μl 0.1M NaHCO₃ pH9.2 and combined with 3.5 mg TAMRA 5-NHS ester which had been dissolved in 400 μl DMF. The reaction proceeded at ambient temperature overnight. The reaction was diluted to 10 ml with water and was purified on a HR10/10 Mono Q column with a 0.1M TEAB/25% MeCN to 1M TEAB/25% MeCN gradient. The fractions containing product were concentrated to remove the acetonitrile and were applied to a Xterra RP C18 19×100 column and eluted with a 0-40% 0.1M TEAB/acetonitrile gradient. The fractions containing pure product were concentrated to dryness and coevaporated 2 times with methanol. HPLC: Xterra RP 4.6× 150 mm, 0.1M TEAA/acetonitrile gradient. Purity 99% Yield 450 nmoles It is noted that similar nucleotide compounds with dyes or other detectable moieties attached to the terminal phosphate could also be made using similar methods to those described in Examples 1-5 above. These include ribonucleotides, deoxyribonucleotides, nucleoside-tetraphosphates, nucleotides with any of the naturally-occurring bases (adenine, guanine, cytosine, thymine, hypoxanthine and uracil) as well as modified bases or modified sugars.

Examples 6 and 7 below demonstrate that dideoxynucleotides having a dye derivative attached to the terminal phosphate may be effectively incorporated as substrates into a growing nucleic acid chain by a nucleic acid polymerase in a template-directed process for detection of a nucleic acid.

Example 6

Nucleic Acid Sequence Detection Using Polymerase Incorporation of Gamma Phosphate-labeled ddGTP Reactions were assembled at room temperature (23° C.) using the dideoxynucleotide of Example (1). Reactions contained primer-template combinations having a single oligonucleotide primer (represented by SEQ ID NO: 1) annealed to one of two different oligonucleotide templates with either a dC or a dT as the next template nucleotide adjacent the 3' terminus of the primer, corresponding to SEQ ID NO: 2 and SEQ ID NO: 3, respectively.

```
5' Cy5 -GTTCTCGGCATCACCATCCG              (SEQ ID NO: 1)

CAAGAGCCGTAGTGGTAGGCCGCTGTTGGTCTATTCCCAC    (SEQ ID NO: 2)

CAAGAGCCGTAGTGGTAGGCTGCTGTTGGTCTATTCCCAC    (SEQ ID NO: 3)
```

Referring now to FIG. 1, for template 1 (SEQ ID NO: 2) in the present example, DNA polymerase would be expected to extend the primer with labeled ddGTP. Similarly, for template 2 (SEQ ID NO: 3) in FIG. 1, DNA polymerase would be expected to extend the primer with ddATP, but not with labeled ddGTP.

Reaction conditions: A 70 μl reaction containing 25 mM Tris, pH 8.0, 5% glycerol 5 mM MgCl₂, 0.5 mM beta-mercaptoethanol, 0.01% tween-20, 0.25 units shrimp alkaline phosphatase, 100 nM primer annealed to template (the next template nucleotide is either dCMP or dTMP, as indicated), and 2 μM ddGTP-CF₃-Coumarin was assembled in a quartz fluorescence ultra-microcuvet in a LS-55 Luminescence Spectrometer (Perkin Elmer), operated in time drive mode. Excitation and emission wavelengths are 390 nm and 500 nm respectively. Slit widths were 5 nm for excitation slits, 15 nm for emission slits. The reaction was initiated by the addition of 0.35 μl (11 units) of a cloned DNA polymerase I genetically engineered to eliminate 3'-5' exonuclease activity, 5'-3' exonuclease activity and discrimination against dideoxynucleotides and 0.25 mM MnCl₂.

As shown in FIG. 1, for reactions containing the gamma labeled ddGTP, dye emission was detected only with Primer: Template 1, where the next nucleotide in the template was a dC. Cleavage of the pyrophosphate product of phosphoryl transfer by shrimp alkaline phosphatase leads to a detectable change in the CF₃-coumarin label which allows for the detection of the nucleic acid. No detectable dye emission was obtained with Primer: Template 2.

Example 7

Nucleic Acid Sequence Detection Using Polymerase Incorporation of Gamma Phosphate-labeled ddATP Reactions were assembled at room temperature (23° C.) using the dideoxynucleotide of Example (2). Reactions contained primer: template combinations having a single oligonucleotide primer (SEQ ID NO: 1) annealed to one of two different oligonucleotide templates with either a dC or a dT as the template nucleotide, adjacent to the 3' terminus of the primer, corresponding to SEQ ID NO: 2 and SEQ ID NO: 3, respectively.

Figure 2:
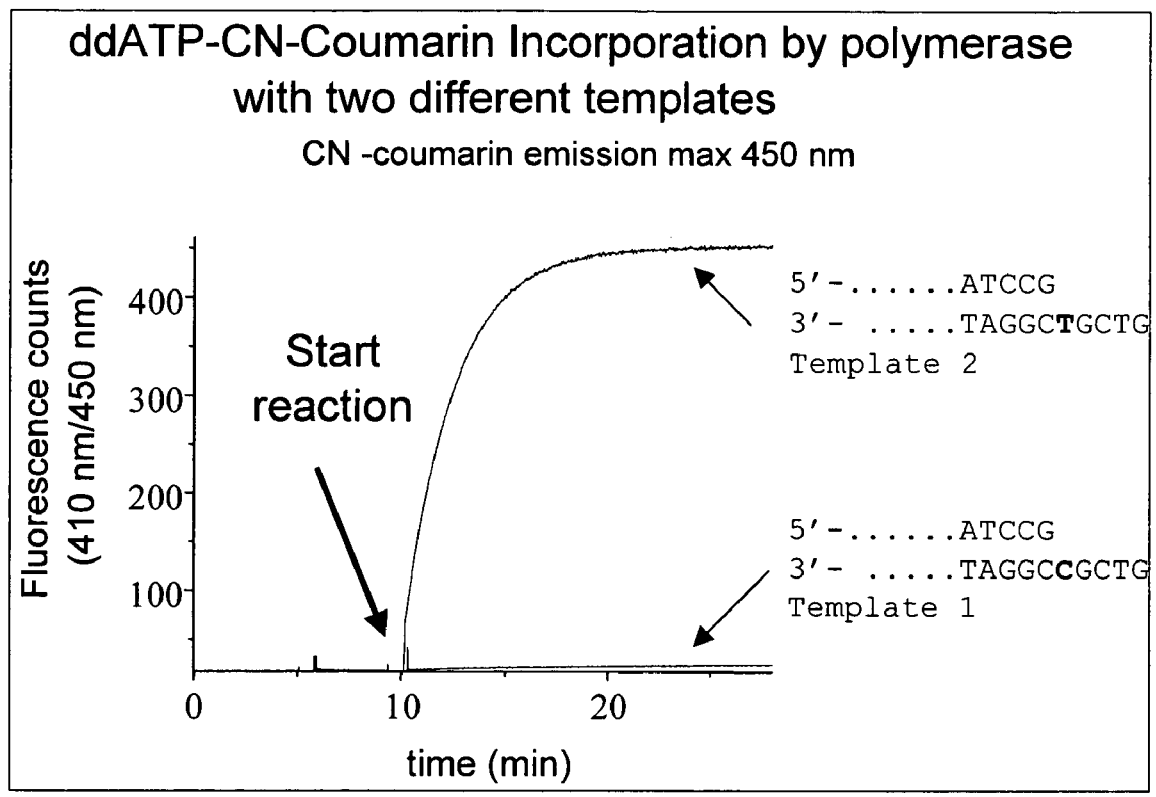
FIG. 2 is a graph showing fluorescence obtained by polymerase utilization of a gamma-phosphate-labeled ddATP in a template-directed process in the presence of phosphatase.

Referring now to FIG. 2, for template 2 (SEQ ID NO: 3) in the present example, DNA polymerase would be expected to extend the primer with labeled ddATP. Similarly, for template 1 (SEQ ID NO: 2) in FIG. 2, DNA polymerase would be expected to extend the primer with ddGTP, but not with labeled ddATP.

Reaction conditions: A 70 μl reaction containing 25 mM Tris, pH 8.0, 5% glycerol 5 mM MgCl₂, 0.5 mM beta-mercaptoethanol, 0.01% tween-20, 0.25 units shrimp alkaline phosphatase, 100 nM primer annealed to template, and 2 μM ddATP-CN-Coumarin was assembled in a quartz fluorescence ultra-microcuvet in a LS-55 Luminescence Spectrometer (Perkin Elmer), operated in time drive mode. Excitation and emission wavelengths are 410 nm and 450 nm respectively. Slit widths were 5 nm for excitation slits, 15 nm for emission slits. The reaction was initiated by the addition of 0.35 μl (11 units) of a cloned DNA polymerase I genetically engineered to eliminate 3'-5' exonuclease activity, 5'-3' exonuclease activity and discrimination against dideoxynucleotides and 0.25 mM $MnCl_2$.

As shown in FIG. 2, for reactions containing the gamma labeled ddATP, dye emission was detected only for Primer: Template 2, where the next nucleotide in the template was a dT. Cleavage of the pyrophosphate product of phosphoryl transfer by shrimp alkaline phosphatase produces a detectable change in the CN-coumarin label that allows one to detect the nucleic acid. No detectable dye emission was obtained with Primer: Template 1.

Examples 8-13 demonstrate the importance of manganese in nucleic acid polymerization reaction using terminal-phosphate labeled nucleoside polyphosphates

Example 8

Relative Incorporation Rates of Phosphate Labeled Nucleotides Versus Base Labeled Nucleotides in Buffers Containing Magnesium or Manganese Reactions (10 μl, 50 degrees C., 10 minutes) contained 1× reaction buffer (25 mM HEPES 8.5, 0.01% tween-20), 3 μg activated DNA (Chromosomal DNA), 5 mM either $MnCl_2$ (circles) or $MgCl_2$ (squares), 1 μM either FAM-TAM-11-ddTTP (dashed lines) or ddT4P-DDAO (solid lines), with a serial 4 fold dilution of Thermo Sequenase I™ DNA polymerase from 10 units per reaction down to 0.01 units per reaction. Results (FIG. 3) were plotted out both on a linear scale and logarithmic scale to show both linearity with enzyme and relative incorporation efficiency. Results indicate a 1.4 fold drop in efficiency of incorporation of the base-labeled nucleotide in the manganese buffer relative to the magnesium buffer, but a 28 fold increase in incorporation efficiency with phosphate-labeled nucleotide in the manganese buffer relative to the magnesium buffer.

Example 9

Effect of Manganese Chloride at Various Concentration on Incorporation of dGTP-DAH-REG in the Presence of 5 mM Magnesium Chloride Following reaction mixtures were prepared: 200 nM dGTP-DAH-REG (DAH=diaminoheptyl linker), 100 nM primer/template, 0.01 mg/ml Phi 29 exo-, 25 mM Tris pH 8, 50 mM KCl, 1 mM beta mercaptoethanol, 0.25 units of shrimp alkaline phosphatase, 5 mM $MgCl_2$ and various concentrations of $MnCl_2$. Incorporation rate was measured by measuring the change in slope of REG fluorescence as the REG-pyrophosphate is released. FIG. 4 clearly shows significant enhancement of rate by addition of $MnCl_2$ in the concentration range investigated.

Example 10

Nucleic Acid Synthesis in the Presence of $MnCl_2$ Without Added $MgCl_2$

Figure 5:
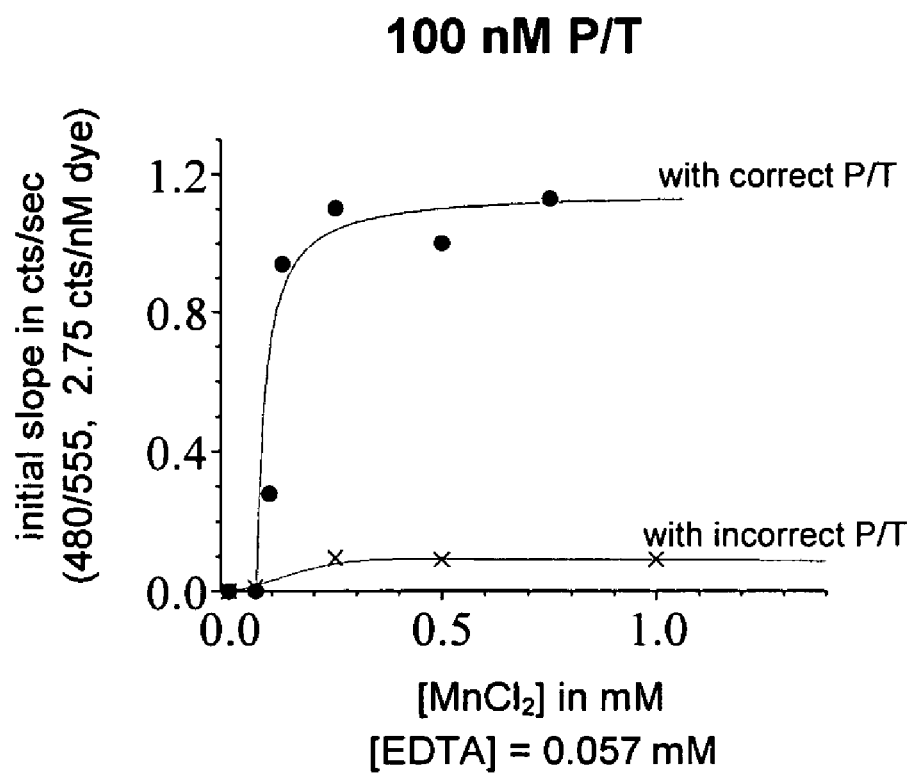
FIG. 5 is a graph showing the incorporation of terminal-phosphate labeled nucleotides in the presence of MnCl$_2$ alone at different concentrations.

Using the procedure described above, rate of incorporation of dGTP-DAH-REG was measured using a primer (SEQ ID NO: 1) and correct and incorrect templates 1 and 2 (SEQ ID NO: 2 and SEQ ID NO: 3 respectively). As FIG. 5 shows with correct template rate is much higher than with the mismatched template.

Example 11

Fidelity of Incorporation of dCTP-DAH-ROX

Using the same primer as in example 9 and template (SEQ ID NO: 4), incorporation of dCTP-DAH-ROX at various times after the reaction was initiated, was investigated. Assay conditions were as follows: Total reaction volume: 30 ul containing 100 nM primer/template, 100 nM Phi 29 exo-polymerase, 50 mM Tris pH 7.5, 75 mM KCl, 0.7 mM $MnCl_2$, 0.1 mM DTT, 0.3 mg/ml BSA. Reaction was initiated by addition of ROX-dCTP to a conc. of 25 uM. Products were separated on a gel, which clearly shows a single base extension and no further incorporation of dCTP-DAH-ROX indicating that even under forcing conditions, no misincorporation takes place.

```
5' Cy5 -GTTCTCGGCATCACCATCCG            (SEQ ID NO: 1)

CAAGAGCCGTAGTGGTAGGCGACTGTTGGTCTATTCCCAC    (SEQ ID NO: 4)
```

Example 12

Effect of $MnCl_2$ on Incorporation of Terminal-phosphate Labeled Nucleotides by Various Polymerases Oligo dT (35mer) was annealed with poly dA by mixing equal volumes of each at 20 uM conc, and incubating at 80° C. for 4 min and instant cooling on ice. 1 ul of this solution was mixed into a 20 ul reaction containing 25 mM Hepes, pH 8.0, 0.01% Tween-20, 10 uM dT4P-DDAO, 0.005 u/ul BAP, a polymerase at concentrations shown in FIG. 7 and various concentrations of $MnCl_2$ and $MgCl_2$. Reactions were incubated at 60° C. for 15 or 30 minutes as shown in FIG. 7. FIG. 7 clearly shows that with all the polymerases tested $MnCl_2$, either alone or in the presence of $MgCl_2$, has a major positive impact on the rate of incorporation. In fact in the absence of $MnCl_2$ rate is extremely slow.

Example 13

Extended Synthesis Using All Four Gamma Labeled dNTP's

Using the same primer/template (SEQ ID NO: 1 and SEQ ID NO: 2) as for example 9 following reaction was assembled: Reaction volume 70 ul, containing 25 mM Tris, pH 8.0, 50 mM KCl, 0.7 mM MnCl2, 0.5 mM beta-mercaptoethanol, 0.1 mg/ml BSA, 0.005 unit/ul SAP, 75 nM each

```
5' Cy5 -GTTCTCGGCATCACCATCCG            (SEQ ID NO: 1)

Figure 8:
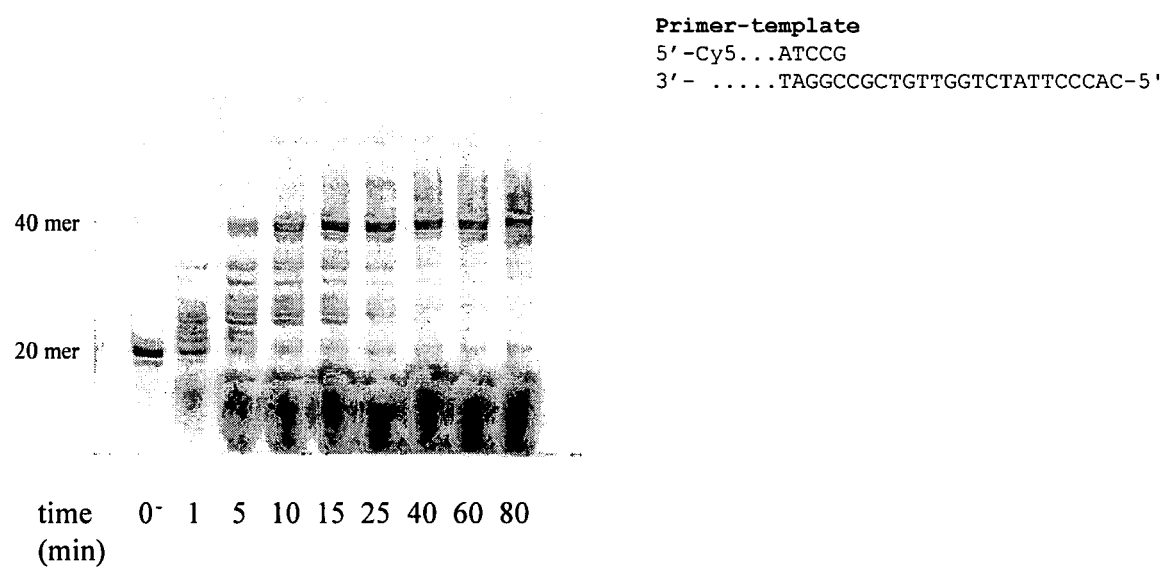
FIG. 8 is a gel file showing the synthesis of a 40 mer DNA using 20 mer oligonucleotide primer and a 40 mer oligonucleotide as a template using all four terminal-phosphate labeled nucleotides in the presence of MnCl$_2$.

CAAGAGCCGTAGTGGTAGGCCGCTGTTGGTCTATTCCCAC    (SEQ ID NO: 2)
``` primer and template, 1 uM each DDAO-dNTP (where N=A, T, G, C) and 6 ul of 0.12 mg/ml Phi 29 exo-polymerase to start the reaction. As shown in FIG. 8, nucleic acid synthesis proceeds to completion by ca 30 minutes. Little or no synthesis occurs in the absence of manganese.

Example 14

Figure 9:
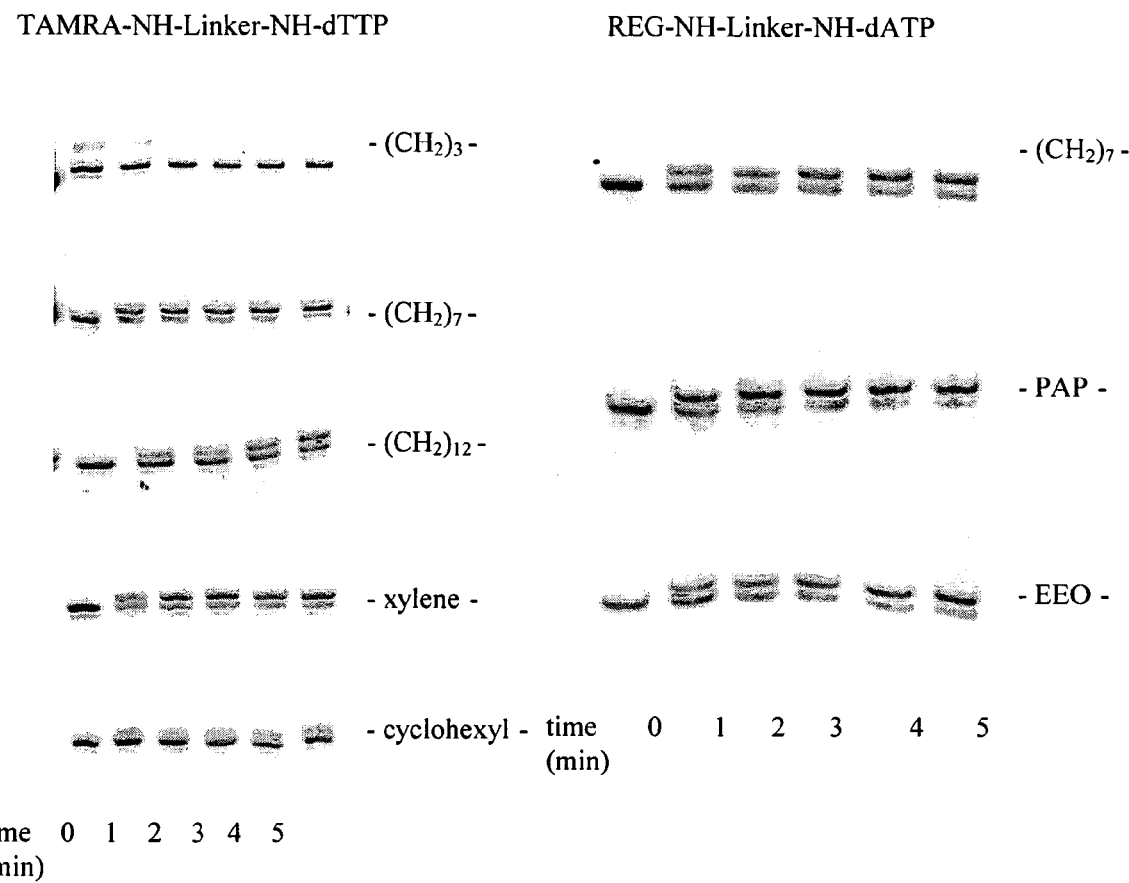
FIG. 9 shows the effect of various linkers on the amount of incorporation of terminal-phosphate labeled nucleotides with linkers.

Effect of Linkers on the Incorporation Rate of Terminal-phosphate Labeled Nucleoside Polyphosphates Containing a Linker Between the Label and the Terminal Phosphate Following terminal-phosphate labeled nucleotides with various linkers were investigated: TAMRA-NH-linker-NH-dTTP (2'-deoxythymidine derivative) and REG-NH-linker-NH-dATP. Linkers are shown in FIG. 9 along with data obtained. Primer and template sequences are those as described in example 9 except the template base at the site of incorporation was varied depending on the base of the incoming nucleotide (Sequence ID 1, 3 and 5).

```
5' Cy5 -GTTCTCGGCATCACCATCCG              (SEQ ID NO: 1)

CAAGAGCCGTAGTGGTAGGCTGCTGTTGGTCTATTCCCAC  (SEQ ID NO: 3)

CAAGAGCCGTAGTGGTAGGCAGCTGTTGGTCTATTCCCAC  (SEQ ID NO: 5)
```

70 ul samples were prepared to contain 25 mM Tris, pH 8.0, 50 mM KCl, 5% glycerol, 1 mM beta-mercaptoethanol, 0.25 units SAP, 0.5 mM MgCl$_2$, 0.125 mM MnCl$_2$, 100 nM primer/template, 1 uM nucleotide and 150 nM ΔTts polymerase and were incubated at 30° C. Reaction mixtures were run on a gel at different times to determine the amount of incorporation. As can be seen terminal-phosphate labeled nucleoside triphosphate with short linker (dioxypropane) is not well accepted by the polymerase. Rest are accepted to different degrees with heptyl being the best.

Example 15

Effect of Adding Polypeptide to the Linker Between the Terminal Phosphate and the Dye Moiety on the Incorporation Rate with Different DNA Polymerases The rate of incorporation of the optimal linker attached dNTP (NH(CH$_2$)$_7$NH between the terminal phosphate and the dye moiety) was compared with the additional penta-lysine attached dNTP. A number of different DNA polymerases were used in the study to ascertain the effect of lysine moieties in the linker on the incorporation of nucleotides. The reactions were carried out as outlined below and the results are presented in Table 5, below.

| Enzyme (rates = nM/min) | dTTP-C7-TAMRA | dTTP-C7-Lys5-TAMRA |
|---|---|---|
| Thy B | 1.29 | 17 |
| Phi-29 D12A | 2 | 0.66 |
| Sequenase | 0.2 | 3 |

-continued

| Enzyme (rates = nM/min) | dTTP-C7-TAMRA | dTTP-C7-Lys5-TAMRA |
|---|---|---|
| Klenow exo- | 0.2 | 1.6 |
| ThermoSequenase I | 0.2 | 9 |
| AMV | 0.2 | 0.2 |
| 9° N-exo- (NEN) | 6 | 0.86 |
| Tsp JS1 (WO 2003/004632) | 0.2 | 13 |
| delta-T10 | 6.2 | 11 |
| Pfu | 4 | 2.6 |
| Tsu | 1.00 | 2 |
| Tne | 2.3 | 20 |
| Ttm | 1.2 | 4 |
| Human pol beta | 5.6 | 300 |

```
5' Cy5- GTTCTCGGCATCACCATCCG              (SEQ ID NO: 1)

CAAGAGCCGTAGTGGTAGGCAGCCGTTGGTCTATTCCCAC  (SEQ ID NO: 5)
```

The reaction mixture contained 10 nM Cy5-20mer primer (SEQ ID NO: 1) and 40mer oligonucleotide template (SEQ ID NO: 5, shown above), 20 mM Tris-HCl, 0.01% Tween 20, 5 mM MgCl$_2$, 0.5 mM MnCl$_2$, 1 mM DTT, Bacterial alkaline phosphatase (BAP) and 100 mM terminal phosphate labeled nucleotide and DNA polymerase.

a. All components with the exception of DNA polymerase were combined and incubated in the presence of 0.0015 U/ul of BAP for 5 minutes at the 25° C. to hydrolyze any unlabeled nucleotides.

b. 1 ul of the reaction mix removed as a time=0 point and quenched in 4 ul of 95% formamide/25 mM EDTA c. 1 ul of DNA polymerase was added to initiate the reaction. 2 ul aliquots at different time points were taken (for rapid time courses at 15, 30, and 60 sec) and were quenched in 8 ul 95% formamide/25 mM EDTA.

d. Samples were denatured in a boiling water bath for 4 min, quick chilled on ice and 2 ul was loaded on a 25% (19:1-Acrylamide: Bisacylamide), 8M Urea, 1×TBE PAGE. Gels were run for approximately 1 hr at 500V.

e. DNA products were visualized on Storm 860 and quantitated by calculating the fraction of the total 20mer primer converted to 21mer product.

It is clear from the table 5 above that penta-lysine linked nucleotide is incorporated much more efficiently than the C7 linked nucleotide by different polymerases.

Example 16

Comparison of Rate of Incorporation of Tri-, Tetra-, and Penta-phosphates Without Linker and With C7 or TEG Linker Between the Dye and Terminal Phosphate Using Phi29 DNA Polymerase The following primer/template were used, A (for deoxyguanosine analog, SEQ ID NO: 1 and SEQ ID NO: 2) and B (for Thymidine Analogs, SEQ ID NO: 1 and SEQ ID NO: 5)

```
A)   5' Cy5 -GTTCTCGGCATCACCATCCG            (SEQ ID NO: 1)
     CAAGAGCCGTAGTGGTAGGCCGCTGTTGGTCTATTCCCAC (SEQ ID NO: 2)

B)   5' Cy5-GTTCTCGGCATCACCATCCG             (SEQ ID NO: 1)
     CAAGAGCCGTAGTGGTAGGCAGCCGTTGGTCTATTCCCAC (SEQ ID NO: 5)
```

Same procedure was used as reported above in example 15. The results are provided in Table 6, below.

| Nucleotide | Rate (nM/min) |
|---|---|
| 1. dTTP-NH(CH$_2$)$_7$-NH-TAMRA | 1.96 |
| 2. dTTP-TEG-NH-TAMRA | 6.48 |
| 3. dT4P-NH(CH$_2$)$_7$-NH-TAMRA | 5.36 |
| 4. dT4P-NH(CH$_2$)$_7$-NH-Alexa488 | 16 |
| 5. dT4P-TEG-NH-Alexa488 | 25 |
| 6. dG4P-Ethylfluorescein | 9.1 |
| 7. dG5P-Ethylfluorescein | 17.6 |

This data clearly shows that additional phosphates in the linker enhance incorporation rate, e.g., compound 3 vs 1. Furthermore, TEG linker is better than diaminoheptyl (NH(CH$_2$)$_7$NH) linker, compound 2 vs 1 and compound 5 vs 4. Additional negative charges on the dye also enhance incorporation rate, compound 4 vs 3 (negative charges on the dye).

Those skilled in the art having the benefit of the teachings of the present invention as set forth above, can effect numerous modifications thereto. These modifications are to be construed as being encompassed within the scope of the present invention as set forth in the appended claims.

What is claimed is:

1. A method of increasing the rate of an enzyme catalyzed nucleoside monophosphate transfer from a terminal-phosphate-labeled nucleoside polyphosphate to detect the activity of said enzyme or said terminal-phosphate-labeled nucleoside polyphosphate, said method comprising:
   a) conducting said enzyme catalyzed nucleoside monophosphate transfer from a terminal-phosphate-labeled nucleoside polyphosphate reaction in reaction buffer comprising a manganese salt, thereby increasing the rate of said reaction over the rate of said reaction in the absence of manganese;
wherein said enzyme is a template dependent DNA polymerase,
further wherein said reaction is conducted in a template dependent manner.

2. The method of claim 1, wherein the polymerase is selected from Phi 29 DNA polymerase, Klenow exo⁻, T7 DNA polymerase exo⁻, Taq DNA polymerase, Taq F667Y deletion 1-235 DNA polymerase, *Thermus thermophilus* F667Y D18A DNA polymerase, Taq F667Y D18A E681M DNA polymerase, *T. hypogea* (Thy B) DNA polymerase, *T. neapolitana*(Tne) DNA polymerase, *T. subterranea* (Tsu) DNA polymerase, *T. barossii* (Tba) DNA polymerase, *T. litoralis* DNA polymerase, *T. kodakaraensis* DNA polymerase, *P. furiosis* DNA polymerase, P. GB-D DNA polymerase, Human Pol beta, Tsp JS1, AMV-reverse transcriptase, MMLV-reverse transcriptase and HIV-reverse transcriptase.

3. The method of claim 1, wherein the concentration of manganese salt is at least 0.01 mM.

4. The method of claim 1, wherein the manganese salt concentration is between 0.01 to 50 mM.

5. The method of claim 1, wherein the manganese salt concentration is between 0.1 to 10 mM.

6. The method of claim 1, wherein an additional metal salt other than manganese, is also present with the terminal-phosphate labeled nucleoside polyphosphate.

7. The method of claim 6, wherein said additional metal salt is a magnesium or a calcium salt.

8. The method of claim 6, wherein said additional metal salt is present at a concentration of 0.01 mM to 50 mM.

9. The method of claim 1, further comprising conducting said reaction in the presence of a metal ion buffer to modulate the concentration of free metal ion.

10. The method according to claim 9, wherein said metal ion buffer is a dicarboxylic acid.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 1
gttctcggca tcaccatccg                                                 20

<210> SEQ ID NO 2
<211> LENGTH: 40
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 2
caagagccgt agtggtaggc cgctgttggt ctattcccac                           40

<210> SEQ ID NO 3
<211> LENGTH: 40
<212> TYPE: DNA
<213> ORGANISM: ARTIFICIAL SEQUENCE
<220> FEATURE:
<223> OTHER INFORMATION: SYNTHETIC OLIGONUCLEOTIDE
```

-continued

```
<400> SEQUENCE: 3
caagagccgt agtggtaggc tgctgttggt ctattcccac                              40

<210> SEQ ID NO 4
<211> LENGTH: 40
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 4
caagagccgt agtggtaggc gactgttggt ctattcccac                              40

<210> SEQ ID NO 5
<211> LENGTH: 40
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 5
caagagccgt agtggtaggc agctgttggt ctattcccac                              40
```